US 9,089,516 B2

(12) United States Patent
Dimmock

(10) Patent No.: US 9,089,516 B2
(45) Date of Patent: *Jul. 28, 2015

(54) METHOD OF PREVENTING OR TREATING INFLUENZA A VIRAL INFECTION USING CLONED DI INFLUENZA A VIRAL PARTICLES

(71) Applicant: The University of Warwick, Coventry (GB)

(72) Inventor: Nigel Dimmock, Coventry (GB)

(73) Assignee: The University of Warwick, Coventry (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/712,045

(22) Filed: Dec. 12, 2012

(65) Prior Publication Data

US 2013/0164264 A1 Jun. 27, 2013

Related U.S. Application Data

(63) Continuation of application No. 12/302,194, filed as application No. PCT/GB2007/001889 on May 24, 2007, now Pat. No. 8,435,508.

(30) Foreign Application Priority Data

May 24, 2006 (GB) .................................. 0610342.8
Oct. 2, 2006 (GB) .................................. 0619445.0

(51) Int. Cl.
*A61K 35/12* (2006.01)
*A61K 39/145* (2006.01)
*A61K 35/76* (2015.01)
*C07K 14/005* (2006.01)
*C12N 7/00* (2006.01)
*A61K 39/00* (2006.01)

(52) U.S. Cl.
CPC .............. *A61K 39/145* (2013.01); *A61K 35/76* (2013.01); *C07K 14/005* (2013.01); *C12N 7/00* (2013.01); *A61K 2039/5252* (2013.01); *A61K 2039/542* (2013.01); *A61K 2039/543* (2013.01); *C12N 2760/16121* (2013.01); *C12N 2760/16122* (2013.01); *C12N 2760/16134* (2013.01)

(58) Field of Classification Search
USPC ......................................................... 424/93.2
IPC ................................................... A61K 48/005
See application file for complete search history.

(56) References Cited

U.S. PATENT DOCUMENTS

| 2006/0057116 A1 | 3/2006 | Kawaoka et al. |
| 2009/0191158 A1 | 7/2009 | Dimmock |
| 2011/0243896 A1 | 10/2011 | Dimmock |

FOREIGN PATENT DOCUMENTS

| GB | 2437799 B | 8/2008 |
| WO | WO2006/051069 A | 5/2006 |
| WO | WO2007/135420 A2 | 11/2007 |

OTHER PUBLICATIONS

Duhaut (J. Virological Methods, 2003, vol. 108, p. 75-82.*
Barrett (Curr. Top. Microbiol. Immunol., 1986, vol. 128, p. 55-84).*
Roux, Adv Virus Res, 1991, vol. 40, p. 181-211.*
Dimmock ("Antiviral activity of defective . . . ", Viral and Other Infections of the respiratory tract, 1996, Myint Ed., London: Chapman & Hall, p. 421-445).*
Mann (Vaccine, Mar. 2006, vol. 24, p. 4290-4296).*
Dimmock (J. General Virology, May 2006, vol. 87, p. 1259-1265).*
Noble (Vaccine, 2004, vol. 22, p. 3018-3025).*
Owen T. Gorman, et al.; "Evolution of Influenza A Virus PB2 Genes: Implications for Evolution of the Ribonucleoprotein Complex and Origin of Human Influenza A Virus"; Oct. 2009; Journal of Virology, vol. 64, No. 10; pp. 4893-4902.
S. Noble, et al.; "Characterization of Putative Defective Interfering (DI) A/WSN RNAs Isolated from the Lungs of Mice Protected from an Otherwise Lethal Respiratory Infection with Influenza Virus A/WSN (H1N1): A Subset of the Inoculum DI RNAs"; Department of Biological Sciences, University of Warwick, UK; Virology 210, pp. 9-19; (1995).
P. Jennings, et al.; "Does the Higher Order Structure of the Influenza Virus Ribonucleoprotein Guide Sequence Rearrangements in Influenza Viral RNA?"; Laboratory of Molecular Biology Medical Research Council Centre, England; vol. 34, pp. 619-627; Sep. 1983.
Mitnaul, Lyndon J. et al., "Balanced hemagglutinin and neuraminidase activities are critical for efficient replication of influenza A virus," Journal of Virology, v. 74, n. 13, Jul. 2000, p. 6016.
Mann et al, "Interfering vaccine (defective interfering influenza A virus) protects ferrets from influenza, and allows them to develop solid immunity to reinfection," Vaccine, Butterworth Scientific. Guildford, GB, v. 24, n. 20, May 15, 2006, p. 4291.
Dimmock, Nigel J. et al., "In vivo antiviral activity: defective interfering virus protects better against virulent Influenza A virus than avirulent virus," Journal of General Virology, v. 87, n. Part 5, May 1, 2006, pp. 1259-1265.
Pattnaik et al.; "Infectious Defective Interfering Particles of VSV from Transcripts of a cNDA Clone"; Cell 1992, vol. 69, pp. 1011-1120.
Duhaut, S.D. et al., "Defective influenza A virus generated entirely from plasmids: Its RNA is expressed in infected mouse lung and modulates disease," Journal of Virological Methods, v. 108, n. 1, Mar. 2003, pp. 75-82.

(Continued)

*Primary Examiner* — Michael Wilson
(74) *Attorney, Agent, or Firm* — King & Schickli, PLLC

(57) ABSTRACT

Cloned, i.e. defined, defective interfering (DI) influenza A virus is produced in embryonated hens eggs using a method which generates large quantities of DI virus material. Co-administration of cloned DI influenza A virus with a lethal dose of virulent influenza A virus conferred protection in mice compared to a control of inactivated cloned DI influenza A virus. Control mice which received only cloned DI influenza A virus and no lethal challenge of virulent influenza A virus were not protected three weeks later on lethal challenge with infective virus. Cloned DI influenza A virus of one subtype is found to act in vivo as an effective antiviral against the same or any other sub-type of influenza A virus. The antiviral effect has been found to have both a therapeutic and a prophylactic application against influenza A infection in humans, mammals and birds.

9 Claims, 6 Drawing Sheets

(56) References Cited

OTHER PUBLICATIONS

Duhaut, S.D. et al., "Defective segment 1 RNAs that interfere with production of infectious influenza A virus require at least 150 nucleotides of 5' sequence: Evidence from a plasmid-driven system," Journal of General Virology, v. 83, n. 2, Feb. 2002, pp. 403-411.
Duhaut, S.D. et al., "Approximately 150 Nucleotides from the 5' End of an Influenza A Segment 1 Defective Viron RNA Are Needed for Genome Stability during Passage of Defective Virus in Infected Cells, "Virology, v. 275, n. 2, Sep. 30, 2000, pp. 278-285.
International Search Report for International Application No. PCT/GB2007/001889, 10 pgs.
Lamb et al. "Orthomyxoviridae: The Viruses and Their Replication", Fields Virology, Third Edition, p. 1353-1395.
Von Magnus, "Propagation of the PR8 Strain of Influenza A Virus in Chick Embryos. III. Properties of the Incomplete Virus Produced in Serial Passages of Undiluted Virus", Acta Pathol. Microbiol. Scand. 1951, vol. 29, p. 157-181.
Nayak et al. "Defective-Interfering (DI) RNAs of Influenza Viruses: Origin, Structure, Expression, and Interference", Current Topics in Microbiology and Immunology 1985, vol. 114, p. 103-151.
Noble et al. "Defective Interfering Type A Equine Influenza Virus (H3N8) Protects Mice from Morbidity and Mortality Caused by Homologous and Heterologous Subtypes of Influenza A Virus", Journal of General Virology 1994, vol. 75, p. 3485-3491.
Noble et al. "Interfering Vaccine: A Novel Antiviral that Converts a Potentially Virulent Infection into one that is Subclinical and Immunizing", Vaccine 2004, vol. 22, p. 3018-3025.
Meier-Ewert et al. "The Role of the Neuraminidase of the Infecting Virus in the Production of Noninfectious (Von Magnus) Influenza Virus", Virology 1970, vol. 42, p. 794-798.
Fazekas et al. "The Production of Incomplete Virus Particles Among Influenza Strains Experiments in Eggs", Brit J. Exp. Path. 1954, vol. 35, p. 60-74.
Holland, "Generation and Replication of Defective Viral Genomes", Virology 1990B 2nd Edition Chapter 6, p. 77-99.
Holland, "Defective Viral Genomes", Virology 1990A 2nd Edition Chapter 8, p. 151-165.
Huang et al. "Defective Viral Particles and Viral Disease Processes", Nature (Lond) 1970, col. 226, p. 325-327.
Dimmock, "Antiviral Activity of Defective Interfering Influenza Virus in Vivo", Viral and Other Infections of the Human Respiratory Tract. 1996, Edited by S. Myint and D.Taylor-Robinson. Published in 1996 by Chapman & Hall ISBN 0 412 60070 6, p. 421-445.
Neumann et al. "Generation of Influenza A Viruses Entirely from Cloned cDNAs". Proc. Natl. Acad. Sci. Aug. 1999, vol. 96, p. 9345-9350.
Marriott, et al.; "Defective Interfering Viruses and Their Potential as Antiviral Agents"; Rev. Med. Virol. 2010, vol. 20, pp. 51-62.
Carter et al. "Synthesis of RNA Segments 1-3 During Generation of Incomplete Influenza A (Fowl Plague) Virus", Archives of Virology 1982, vol. 73, p. 109-119.
Murphy et al. "Orthomyxoviruses", Fields Virology 3rd Edition 1996, Chapter 46, p. 1397-1445.
Von Magnus, "Propagation of the PR8 Strain of Influenza A Virus in Chick Embryos. I. The Influence of Various Experimental Conditions of Virus Multiplication", Acta. Pathol. Microbiol. Scand. 1951A, vol. 28, p. 250-277.
Von Magnus, "Propagation of the PR8 Strain of Influenza A Virus in Chick Embryos. II. The Formation of "Incomplete" Virus Following Inoculation of Large Doses of Seed Virus", Acta Pathol. Microbiol. Scand. 1951B, vol. 28, p. 278-293.
Von Magnus, "Incomplete Forms of Influenza Virus", Adv. Virus Res. 1954, vol. 21, p. 59-79.
Von Magnus, "The in Ovo Production of Incomplete Virus by B/Lee and A/PR 8 Influenza Viruses", Arch. Virol. 1965, vol. 17, p. 414-423.
Carter et al. "Incomplete Avian Influenza Virus Contains a Defective Non-Interfering Component", Archives of Virology 1982, vol. 71, p. 13-25.
Clements, "Surface Warfare Against Pathogens Using Mucosal Vaccines", Nature Biotechnology Jul. 1997, vol. 15, p. 622-623.
Walker, "New Strategies for Using Mucosal Vaccination to Achieve More Effective Immunization", Vaccine 1994, vol. 12, No. 5, p. 387-400.
Cane et al. "Intracellular Stability of the Gene Encoding Influenza Virus Haemagglutinin", Virology 1990. vol. 175, p. 385-390.
Duhaut et al. "Heterologous Protection of Mice from a Lethal Human H1N1 Influenza A Virus Infection by H3N8 Equine Defective Interfering Virus: Comparison of Defective RNA Sequences Isolated from the DI Inoculum and Mouse Lung", Virology 1998, vol. 248, p. 241-253.
Subbarao et al. "Evaluation of a Genetically Modified Reassortant H5N1 Influenza A Virus Vaccine Candidate Generated by Plasmid-Based Reverse Genetics", Virology 2003, vol. 305, p. 192-200.
Karber, "Statistical Methods in Virology", Textbook of Virology 5th Edition 1968, Chapter 8, Section 1, p. 104 and p. 118.
Von Magnus, "Studies on Interference in Experimental Inftuenza", Ark. Kemi. Mineral. Geologi. vol. 24N, No. 7, p. 1-6.
McGhee et al. "The Mucosal Immune System: from Fundamental Concepts to Vaccine Development", Vaccine 1992, vol. 10, No. 2, p. 75-88.
Cane et al. "Intracellular Stability of the Interfering Activity of a Defective Interfering Influenza Virus in the Absence of Virus Multiplication", Virology 1987, vol. 159, p. 259-264.
International Search Report for International patent application No. PCT/GB2009/051666 dated Mar. 1, 2010.
Almeida et al. "Nasal Delivery of Vaccines", Journal of Drug Targeting 1996, vol. 3, p. 455-467.
Rott et al. "Untersuchungen Uber Die Hamagglutinierenden-nichtinfektiosen Teilchen Der Inftuenza-Viren", Z. Naturforschg. 1961, 16 b, p. 310-321.

* cited by examiner

AGTAGAAACAAGGTCGTTTTTAAACTATTCGACACTAATTGATGGCCATCC
GAATTCTTTTGGTCGCTGTCTGGCTGTCA GTAAGTATGCTAGAGTCCCGTTTCCGTTTCATTACCAACACCACATCCCCT
TGCCCAATTAGCACATTAGCCTTCTCTCC TTTCGCAAGGTTGCTCAGTTCATTGATGCTTAGTGCTGGCCCATATCTCTT
GTCCTCTTTGCCCAGAATGAGGAATCCCC TCAGTCTTCTCCTGTCTTCCTGATGTGTACTTCTTGATTATGGCCATATGGT
CCACGGTGGTTTTTGTGAGTATCTCGCG

GGTGCGAGACTGCGACATTAGATTTCTTAGTTCTTTTATTCTTTCCATATTG
AATATATTTGACCTGCTTTCGCT

Figure 1

AGTAGAAACAAGGTCGTTTTTAAACTATTCGACACTAATTGATGGCCATCC
GAATTCTTTTGGTCGCTGTCTGGCTGTCA

GTAAGTATGCTAGAGTCCCGTTTCCGTTTCATTACCAACACCACATCCCCT
TGCCCAATTAGCACATTAGCCTTCTCTCC

TTTCGCAAGGTTGCTCAGTTCATTGATGCTTAGTGCTGGCCCATATCTCTT
GTCCTCTTTGCCCAGAATGAGGAATCCCC

TCAGTCTTCTCCTGTCTTCCTGATGTGTACTTCTTGATTATGGCCATATGGT
CCACGGTGGTTTTTGTGAGTATCTCGCG

GGTGCGAGACTGCGACATTAGATTTCTTAGTTCTTTTATTCTTTCCATATTG
AATATAATTGACCTGCTTTCGCT

Figure 2

METHOD OF PREVENTING OR TREATING INFLUENZA A VIRAL INFECTION USING CLONED DI INFLUENZA A VIRAL PARTICLES

This application claims priority as a continuation patent application of U.S. patent application Ser. No. 12/302,194 filed on Nov. 24, 2008, which in turn is a 371 application of PCT patent application No. PCT/GB2007/001889 filed on May 24, 2007 claiming priority to British Patent Appl. Nos. GB0610342.8 filed on May 24, 2006 and GB0619445.0 filed on Oct. 2, 2006, the disclosures of each of which are incorporated herein by reference in their entirety.

FIELD OF THE INVENTION

The invention relates to virology and the prevention and/or treatment of viral infection, particularly influenza A, in animals, including birds and humans. The invention also relates to field of antiviral treatment. The invention further relates to processes for the production of Defective Interfering (DI) virus, i.e. "DI virus", for use as an active agent in the prevention and/or treatment of viral infection. A "DI virus" is a defined, usually cloned, "defective interfering" virus. An "interfering virus" is usually a defective virus which disrupts the normal replication and infection cycle of a non-defective virus. DI influenza virus preparations are already known in the art, but are genetically heterogeneous.

BACKGROUND TO THE INVENTION

The Orthomyxoviridae are a family of RNA viruses which infect vertebrates. The family includes those viruses which cause influenza.

Influenza is a viral infection of the respiratory system characterized by fever, cough, and severe muscle aches. There are three genera of influenza virus, identified by antigenic differences in their nucleoprotein and matrix protein: Influenzavirus A, Influenzavirus B and Influenzavirus C.

Influenza A and B viruses each contain eight segments of single stranded RNA (ssRNA). The viruses comprise major external virion proteins, haemagglutinin (H) and neuraminidase (N), of which there are 16 H subtypes and 9 N subtypes which probably form all 144 possible permutations.

Influenza C virus contains seven segments of ssRNA, because the virus lacks a separate neuraminidase gene (see Lamb, R. and Krug, R. M. (1996) Chapter 45; Orthomyxoviridae: The viruses and their replication—Fields Virology, $3^{rd}$ Edition, Raven Publishers, Philadelphia).

The major causative agent of human influenza is the type A virus. The virus genome consists of eight negative sense, single-stranded RNA segments. The RNA encodes 9 structural and 2 non-structural proteins. These are known to encode the influenza virus proteins as set out below:
Segment 1 encodes the polymerase protein PB2
Segment 2 encodes the polymerase protein PB1
Segment 3 encodes the polymerase protein PA
Segment 4 encodes the haemagglutinin protein (HA).
Segment 5 encodes the neuraminidase protein (NA).
Segment 6 encodes the nucleoprotein (NP).
Segment 7 encodes two matrix proteins (M1 and M2).
Segment 8 encodes two non-structural proteins (NS1 and NS2).

Human influenza viruses A and B are both responsible for seasonal disease in people, but only influenza A viruses cause worldwide pandemics. In human viruses, three distinct haemagglutinins, referred to as H1, H2, and H3 and two distinct neuraminidases, referred to as N1 and N2 have been identified. Viruses are classified by their constituent haemagglutinin and neuraminidase proteins into subtypes. For example, the viral strain which caused the "Spanish" flu pandemic of 1918 belongs to the H1N1 subtype. The H2N2 subtype appeared in 1957 and replaced H1N1; the H3N2 subtype appeared in 1968 and replaced H2N2. Each replacement event is known as an antigenic shift, and results in a pandemic as the entire human population lacks effective immunity to the new virus. Following a shift the major viral H and N surface proteins undergo continuous and progressive antigenic changes called antigenic drift. Drift viruses cause annual epidemics of influenza. Currently the drift descendents of H3N2 and H1N1 (which reappeared in 1977) are co-circulating. Influenza B virus does not cause pandemic influenza but contributes to epidemics.

However, the majority of influenza A viruses exist in various waterfowl, causing subclinical gut infections. For example, in October 2003, an epidemic of influenza in chickens began sweeping through several countries in the Pacific Rim (Vietnam, Thailand, Japan, China, South Korea, Cambodia), and has recently reached Europe. This virus is designated H5N1. The H5 molecule is common among bird influenza viruses but has not been found in influenza viruses that cause human epidemics. However, sporadic human cases of H5N1 (with an alarmingly-high fatality rate) have been occurring ever since and are of significant concern.

Genomic studies suggest that the human pandemic viruses arose from avian viruses adapting to humans (1918), or genetically interacting with an existing human virus (1957 and 1968). Thus, as avian viruses (such as H5N1 and H7N7) move from their natural host into domestic poultry and into close contact with humans, there is concern about an emerging new pandemic virus. However, none of these viruses currently transmits effectively from person-to-person. Highly infectious new pandemic viruses all cause high morbidity and mortality, with 50 million estimated worldwide deaths for 1918 virus and 1-5 million for 1957 and 1968 viruses. Although an influenza infection elicits a strong immune response against the strain that caused it, the speed with which new strains arise by antigenic drift soon leaves a previously infected individual susceptible to a new infection. Influenza vaccines have been available commercially for many years and include killed and live vaccines. Some vaccines contain inactivated virus particles or more usually just the purified H and N components. These vaccines have proved helpful in reducing the extent and severity of influenza epidemics. However, because of the phenomenon of antigenic drift, the influenza strains used as the basis of existing vaccines are reassessed from year to year by WHO and may have to be changed. Also, any new vaccine required for a new pandemic virus would take several months before it could be made available for administration.

Other lines of defense against influenza include antiviral drugs. For example, Amantadine and Rimantadine inhibit the action of one of the matrix proteins needed to get viral RNA into the cytosol. These drugs are effective against all influenza type A viruses (but not type B viruses) but a rapid evolution of resistance to the drugs has been observed.

Alternatively, Zanamivir (Relenza®) and Oseltamivir (Tamiflu®) block neuraminidase and thus act to inhibit the release of progeny virions from infected cells and the spread of infection. However, the effectiveness of these therapies is somewhat limited. Treatment has to be started soon after infection, it is given twice daily, and is only able to shorten the duration of symptoms by one to three days. Virus that is resistant to Tamiflu is being found in patients with influenza.

Another influenza pandemic is inevitable, and is expected to result in widespread morbidity and upwards of a million deaths worldwide, despite developments in vaccinology and antiviral drugs. New measures to combat influenza are urgently needed.

DI viruses have a long history. They were discovered as auto-interfering elements in influenza A virus preparations by von Magnus who studied them in the late 1940s and early 1950s (e.g. von Magnus, P (1947) Ark. Kemi. Mineral. Geol, 24b: 1). For many years these interfering elements were named after him Later, when it was realized that these elements were found almost universally amongst viruses, they were called DI viruses (see e.g. Huang & Baltimore (1970) Nature 226: 325-327). Interest in DI viruses reached a peak in the 1970's but then waned due to an over-extravagant expectation of their in vivo antiviral activity.

All influenza A viruses appear to have a replication apparatus that allows the exchange of genome segments (reassortment) in dually infected cells, giving these viruses immense genetic flexibility. Such an event gave rise to the 1957 and 1968 pandemic viruses. In addition to the normal replication process, mistakes in replication occur that give rise to small RNAs of 400-500 nt lacking around 80% of the central sequence of the template, which appears to result from the polymerase copying the initial part of the template, detaching from the template and then rejoining and copying the other terminus. These small RNAs retain the terminal replication and encapsidation signals, and their small size suggests that more copies can be made in unit time compared with the full-length RNA segment. Encapsidation of genomic RNAs appears to be an organized process so that a virion contains just one copy of each of the 8 segments. A virion does not appear to discriminate between a defective and a full-length RNA, so when defective RNAs are in excess they are preferentially encapsidated. A particle containing the deleted genome segment cannot synthesize the viral protein(s) normally encoded by that RNA, and is non-infectious, although it can be replicated in trans when that cell is infected by an influenza A virus. Incorporation of defective RNAs into virions results in a reduction in the amount of infectious virus produced. Thus virions carrying a deleted genome are known as interfering or defective-interfering (DI) viruses.

Viruses of Orthomyxoviridae family therefore give rise spontaneously to defective RNA segments as a result of an internal deletion (75-80% of the nucleotides) in one or more genomic segments. The DI virus genome is therefore a deleted form of the genome of the infectious virus which gave rise to it; and it has several unique properties which distinguishes it from other types of defective viral nucleic acid molecules (see Dimmock, N. J. (1996) "Antiviral activity of defective interfering influenza virus in vivo"—Viral and other infections of the human respiratory tract; S. Myint and D. Taylor-Robinson (Eds), Chapman & Hall).

Compared to an active, i.e. live or infectious virus, a DI virus is non-infectious and replicates only when its genome is present in a cell which has been infected by a virus with a complete genome (sometimes referred to as a "helper virus"). DI influenza virus is encapsidated into virus particles which are usually indistinguishable in size and protein composition from infectious virus particles.

After arising, de novo, a DI genome is rapidly amplified in concentration relative to that of the genome of the infectious virus, so that within a few infectious cycles (or passages) there is more DI virus in a population than infectious virus.

DI virus has the ability to interfere intracellularly with infectious virus so that it is specifically able to inhibit multiplication of infectious virus.

In vivo animal studies have shown that spontaneously produced DI influenza A virus (A/equine/Newmarket/7339/79 (H3N8)) can, in sufficient amount, protect mice against lethal influenza A challenge with both the homologous virus (EQV) or with heterologous subtypes A/WSN (H1N1) or A/PR/8/34 (H1N1). In these studies the DI virus preparation was UV-treated in order to inactivate any live helper virus present.

A single administration appeared to provide prophylaxis for up to about 5 days. However, these DI virus preparations were heterogeneous and comprised a multiplicity of undefined defective RNA sequences from different genomic segments (see Noble and Dimmock (1994) J. Gen. Virol. 75: 3485-3491).

DI virus A/WSN (H1N1) grown in embryonated eggs protected mice against lethal challenge with A/WSN (H1N1). Comparison of egg-grown DI virus RNA species with DI virus RNA extracted from surviving mouse lungs showed that there were 5 putative RNAs responsible for mouse survival. Each of the five RNA species of the DI virus had an internal deletion (see Noble & Dimmock (1995) Virology 210: 9-19). The 3' and 5' ends of four of these RNA species appeared intact.

Duhaut & Dimmock (2000, Virology 275: 278-285) modified a defective segment 1 RNA of EQV by placing it under the control of a human RNA polymerase I promoter (POLI) in a plasmid. Each of the plasmids encoded an RNA of approximately 400 nucleotides but, due to the exact position of the internal deletion, differing lengths of the 5' and 3' end sequences remained. Vero cells were transfected with each plasmid together with one of three different helper virus subtypes, including the parent (H3N8) or an H2N2 or H1N1 subtype. Serial passage was carried out in cell culture. At least 150 nucleotides at the 5' end of the DI virus RNA were found to be necessary for reliable passage in vitro in each of the cell lines used together with the particular helper viruses used.

It has not been possible to experimentally elucidate the process by which non-cloned DI influenza A viruses reduce the yield of infectious virus, inhibit virus-induced cytopathology, and protect animals from clinical disease, as most populations of DI virus contain many different defective RNA sequences, derived from different genome segments and with a variety of central deletions. Thus the RNA content of such non-cloned populations of defective virus cannot be reproduced effectively, and it has not been possible to analyze the relationship between RNA sequence and antiviral activity.

Duhaut & Dimmock (2002, J. Gen. Virol. 83: 403-411) demonstrated that a DI virus RNA derived from a plasmid system appears to behave authentically in cell culture. One plasmid (POLI-317) gave rise to DI virus RNA that replicated stably in vitro in the presence of helper virus and strongly inhibited the production of the helper virus in that system.

Duhaut & Dimmock (2003, J. Virol. Methods 108: 75-82) described the preparation of a defined (i.e. cloned) DI influenza A virus generated entirely from plasmids which were used to transfect host cells in culture. The plasmids used encoded the DI RNA (H3N8 or H7N7) and infectious influenza virus (A/WSN, H1N1). DI virus generated in this way was passaged once in embryonated chicken's eggs and then administered to mice in the presence of helper virus (H1N1). The cloned DI virus propagated intact into mouse lung. The cloned DI virus (without infectious helper) was also tested for any protective effect in mice against a lethal (H1N1) challenge. Some very weak and short lived prophylactic effect was observed, but this only delayed the onset of clinical symptoms and death in the mice.

Noble et al. (2004, Vaccine 22: 3018-3025) reported an in vivo study in mice using a naturally occurring (i.e. heterogeneous and undefined) DI virus preparation (EQV H3N8).

Administration of this DI virus preparation to mice was found to generate prophylaxis protection for a period, and at the same time converted an otherwise lethal infection into an avirulent and immunizing infection.

Dimmock & Marriott (2006, J. Gen. Virol. 87: 1259-1265) described an apparent anomaly in which a heterogeneous and undefined DI virus preparation solidly protects mice from lethal disease caused by A/PR/8/34 (H1N1) and A/WSN/40 (H1N1) viruses, but only marginally protects from disease caused by A/Japan/305/57 (A/Jap H2H2). A/Jap was found to require 300-fold more infectious units to cause clinical disease in mice than A/PR8. The proportions of DI virus and challenge virus were varied and tested. A conclusion reached was that the efficacy of the DI virus depends on the infectious dose of challenge virus rather than its disease-causing dose.

Mann et al. (2006, Vaccine 24, 4290-4296) tested heterogeneous and undefined DI A/EQV RNAs that had been rescued by (A/PR8) in ferrets. DI virus was administered in two doses followed by challenge with infectious A/Sydney 5/97 (H3N2). Though the infectious challenge was not lethal, the DI virus-treated ferrets showed only occasional and mild clinical symptoms, compared to the control animals which became severely ill.

US2006/0057116 A1 (Kawaoka and Neumann) describes plasmids and a method of transfecting and culturing cells to produce recombinant influenza A virus in vitro in the absence of any helper virus. Specifically, influenza A viruses can be prepared entirely from their cloned cDNAs in transfected cell lines. Mutations can be incorporated into any gene segment.

WO2006/051069 (Solvay Pharmaceuticals & Erasmus University) discloses conditionally defective influenza virus particles and a method of making them. From the starting point of transfected cells not being able to produce large quantities of defective influenza virus particles for use as vaccines, the specification teaches an alternative method. The method involves a cell transfected with 7 RNA segments of the influenza virus and an eighth segment in which a polymerase encoding sequence is deleted. The cell includes a second expression plasmid carrying the sequence of the deleted polymerase. On expression, the transfected cell yields "conditionally" defective virus particles which can only replicate in a cell line expressing the polymerase that is not present in the defective genome. The defective influenza virus particles can only replicate once in suitable, albeit not complemented, host animals or cells. The conditionally defective virus particles are intended for vaccine use or gene delivery purposes and so advantageously the virus particle preparations are unable to replicate in normal cells and contain no wild-type or helper virus.

Although a prototype system has been described (see Duhaut & Dimmock, 2003 supra) for preparing a cloned DI influenza A virus (which turned out to be only weakly protective on one occasion in mice), it does not offer a practical route for preparing the necessary amounts of cloned DI viruses needed for further laboratory investigations, let alone the amount of cloned DI virus that would be needed on a routine basis in order to carry out animal and human clinical trials or provide for prophylaxis and/or therapy in routine, epidemic or pandemic situations.

von Magnus, P. (1951a) *Acta Pathol Microbiol Scand* 28, 250-277; von Magnus, P. (1951b) *Acta Pathol Microbiol Scand* 28, 278-293; von Magnus, P. (1951c) *Acta Pathol Microbiol Scand* 29, 157-181; and von Magnus, P. (1954) *Adv Virus Res* 21, 59-79 each describe standard (i.e. infectious) A/PR8 (H1N1) virus made by inoculation of embryonated chickens eggs with "allantoic fluids diluted $10^{-6}$." On page 158 of von Magnus (1951a) incomplete virus (i.e. DI virus) was made "by serial passages of undiluted allantoic fluids" with "$1^{st}$, $2^{nd}$, $3^{rd}$, etc passages of undiluted virus." Up to 4 passages were made.

Fazekas de St Groth, S. & Graham, D. M. (1954). "The production of incomplete influenza virus particles among influenza strains. Experiments in eggs." *Brit J Exp Path* 35, 60-74. Also, von Magnus, P. (1965) "The in ovo production of incomplete virus by B/Lee and A/PR8 influenza viruses." *Arch Virol* 17, 414-423. These references describe the production of incomplete (DI) B/Lee virus in embryonated chickens eggs. Production usually required 6 or more passages of undiluted virus.

Meier-Ewert, H. & Dimmock, N. J. (1970). "The role of the neuraminidase of the infecting virus in the generation of noninfectious (von Magnus) interfering virus." *Virol* 42, 794-798. This reference describes the production of incomplete (DI) A/Jap/305/57 (H2N2) virus. Table 2 shows how the virus production required 3 serial undiluted passages.

Rott, R. & Schafer, W. (1960) "Untersunchungen uber die hamaggluttinierenden-nichtinfektiosen Teilchen der Influenza-Viren. I. Die Erzeugung von 'inkompletten Formen' beim Virus der klassischen Geflugelpest (v. Magnus Phanomen)" *Zeitschrift fur Naturforschung* 16b, 310-321; and Carter, M. J. & Mahy, B. W. J. (1982). *Arch Virol* 71, 12-25. These references describe how incomplete A/fowl plague virus (H7) was produced by serial passage of culture fluids at high multiplicity—usually undiluted virus. The cell culture fluids were obtained from chick embryo fibroblast cells.

Huang, A. S. & Baltimore, D. (1970) "Defective viral particles and viral disease processes" *Nature* (*Lond*) 226, 325-327. This review article at page 325 describes how the synthesis of DI particles by cells or animal tissues on infection with high multiplicities (or undiluted passage virus) is achieved for Rift Valley fever virus, vesicular stomatitis virus, fowl plague virus, simian virus 40, polyoma virus, lymphocytic choriomeningitis virus, Sendai virus, simian virus 5, and poliovirus.

Holland, J. J. (1990a) "Defective viral genomes" In *Virology,* 2nd edn, pp. 151-165. Edited by B. N. Fields & D. M. Knipe New York: Raven Press. In this review article, page 155 describes how serial undiluted passage of virus in cell culture (or eggs or animals) is still the method of choice for generation of DI particles of any virus.

Holland, J. J. (1990b) "Generation and replication of defective viral genomes" In *Virology,* 2nd edn, pp. 77-99. Edited by B. N. Fields & D. M. Knipe New York: Raven Press. Referring to FIG. 2 this book chapter discloses how DI particle bands did not appear until the fourth (undiluted virus) passage.

Nayak, D. P., Chambers, T. M. & Akkina, R. K. (1985) "Defective-interfering (DI) RNAs of influenza viruses: origin, structure, expression and interference" *Curr Topics Microbiol Immunol* 114, 103-151 is a review article which attests to the production of DI viruses by serial independent undiluted passage of virus.

The cloned DI influenza A virus produced in cell culture does not provide sufficient quantities of cloned virus for practical application. A problem that the invention seeks to solve is how to produce sufficient virus for in vivo studies and for pharmaceutical uses.

The inventor attempted to produce cloned DI influenza A virus by passage in embryonated hens' eggs, but too low a yield of DI virus resulted. A problem that the present invention seeks to solve is therefore how to provide sufficient yield of cloned DI influenza A virus by passage in embryonated eggs.

SUMMARY OF THE INVENTION

Accordingly, the present invention provides a method of producing a cloned DI influenza A virus comprising: (a) transfecting a cell with (i) a plasmid comprising an RNA segment of an influenza A virus that has a deletion therein, and (ii) plasmids which in combination provide RNA segments 1 to 8 of an infectious influenza A virus; (b) culturing the transfected cells for a period; (c)(i) introducing an aliquot of less than 100 μl of the transfected cell culture medium into an embryonated egg; or (ii) taking an aliquot of the transfected cell culture medium and reducing the number or concentration of virus particles in that aliquot and introducing at least a portion of the aliquot into an embryonated egg; or (iii) introducing transfected cell culture medium containing fewer than $4 \times 10^9$ copies of the RNA deletion segment into an embryonated egg; and (d) incubating the egg for a period; and (e) recovering virus material from the egg.

The invention also provides a method of producing a cloned DI influenza A virus comprising: (a) transfecting a cell with (i) a plasmid comprising an RNA segment of an influenza A virus, the segment having a deletion therein, and (ii) plasmids which in combination provide RNA segments 1 to 8 of an infectious influenza A virus; (b) culturing the transfected cells for a period; (c) taking an aliquot of the transfected cell culture medium; (d) introducing at least a portion of that aliquot into an embryonated egg; (e) incubating the egg for a period; (f)(i) introducing into a further embryonated egg an aliquot of less than 100 μl of virus material taken from the incubated egg; or (ii) recovering an aliquot of virus material from the incubated egg and reducing the number or concentration of virus particles in that aliquot and introducing at least a portion of that aliquot into a further embryonated egg; or (iii) introducing into a further embryonated egg virus material containing fewer than $4 \times 10^9$ copies of the RNA deletion segment taken from the incubated egg; (g) incubating the further egg for a period; and (h) recovering virus material from the egg.

The invention also provides a method of producing a cloned DI influenza A virus comprising: (a) transfecting a cell with (i) a plasmid comprising an RNA segment of an influenza A virus that has a deletion therein, and (ii) plasmids which in combination provide RNA segments 1 to 8 of an infectious influenza A virus; (b) culturing the transfected cells for a period; (c) introducing at least a portion of transfected cell culture medium into at least 10 embryonated eggs; (d) incubating at least some of the eggs for a period; and (f) recovering virus material from at least one incubated egg.

The invention further provides a method of producing a cloned DI influenza A virus comprising: (a) transfecting a cell with (i) a plasmid comprising an RNA segment of an influenza A virus, the segment having a deletion therein, and (ii) plasmids which in combination provide RNA segments 1 to 8 of an infectious influenza A virus; (b) culturing the transfected cells for a period; (c) taking an aliquot of the transfected cell culture medium; (d) introducing at least a portion of that aliquot into an embryonated egg; (e) incubating the egg for a period; (f) introducing into at least 10 further embryonated eggs at least a portion of the virus material from the incubated egg; (g) incubating the further eggs for a period; and (h) recovering virus material from at least one egg.

The invention further provides a method of passaging cloned DI influenza A virus, comprising: (a) introducing no more than $4 \times 10^9$ copies of a cloned DI influenza A genome into an embryonated egg; (b) incubating the egg for a period; and (d) recovering virus material from the egg.

In relation to all of the aforementioned methods of the invention producing or passaging cloned DI influenza A virus, at least $1 \times 10^7$ copies of the cloned DI influenza A genome are preferably introduced into an embryonated egg. The preferred range of individual cloned DI influenza A particles, genomes or deleted RNA segment is $1 \times 10^7$ to $4 \times 10^9$. In other preferred aspects, no more than $3 \times 10^9$, $2 \times 10^9$, $1 \times 10^9$, $9 \times 10^8$, $8 \times 10^8$, $7 \times 10^8$, $6 \times 10^8$, $5 \times 10^8$, $4 \times 10^8$, $3 \times 10^8$, $2 \times 10^8$, $1 \times 10^8$, $9 \times 10^7$, $8 \times 10^7$, $7 \times 10^7$, $6 \times 10^7$ $5 \times 10^7$, $4 \times 10^7$, $3 \times 10^7$ or $2 \times 10^7$ particles, genomes or deleted segments are used.

In further preferred aspects, at least $3 \times 10^9$, $2 \times 10^9$, $1 \times 10^9$, $9 \times 10^8$, $8 \times 10^8$, $7 \times 10^8$, $6 \times 10^8$, $5 \times 10^8$, $4 \times 10^8$, $3 \times 10^8$, $2 \times 10^8$, $1 \times 10^8$, $9 \times 10^7$, $8 \times 10^7$, $7 \times 10^7$, $6 \times 10^7$ $5 \times 10^7$, $4 \times 10^7$, $3 \times 10^7$ or $2 \times 10^7$ particles, genomes or deleted segments are used, subject to the above mentioned list of upper limits for particles, genomes or deleted segments.

The inventor has found that 10-fold less, preferably 100-fold less, even 1000-fold less virus material is needs to be inoculated into embryoned eggs (compared to existing teachings in the art) in order to yield practical quantities of cloned DI influenza A virus.

The invention also provides a method of passaging a cloned DI influenza A virus comprising: (a) introducing an aliquot known or suspected of containing a cloned DI influenza A virus particle into an embryonated egg, wherein the volume of the aliquot introduced is less than 100 μl; (b) incubating the egg for a period; and (c) recovering virus material from the egg.

The invention further provides a method of passaging a cloned DI influenza A virus comprising: (a) introducing an aliquot known or suspected of containing a cloned DI influenza A virus particle into at least 10 embryonated eggs; (b) incubating at least some of the eggs for a period; and (c) recovering virus material from at least one incubated egg.

The invention additionally provides a method of passaging a cloned DI influenza A virus comprising: (a) reducing the number or concentration of virus in an aliquot known or suspected of containing a cloned DI virus A particle; (b) introducing at least a portion of the aliquot into an embryonated egg; (c) incubating the egg for a period; and (d) recovering virus material from the egg.

In the relevant embodiments described above, the aliquot of less than 100 μl of culture medium (or aliquot obtained is from an egg) preferably a volume in the range 0.1-100 μl are possible.

The aliquot volume is more preferably less than 50 μl, even more preferably less than 10 μl. Even smaller aliquot volumes of less than 1 μl or less than 0.1 μl are possible.

The invention contemplates aliquot volumes in the range 0.05 μl-10 μl; 0.1 μl-100 μl; 10-100 μl; 0.1 μl-10 μl; 0.1 μl-20 μl or 0.1 μl-50 μl.

The aliquot of less than 100 μl of culture medium (or egg aliquot), or the aliquot as further defined above, may be diluted prior to introducing the whole diluted, or at least a portion of the diluted aliquot, into embryonated eggs.

Overall, the employment of a culture medium (or egg) aliquot of less than 100 μl volume (or as further defined above) results in an inoculum for the embryonated egg whereby a reduced number or concentration of virus particles are present in the inoculum. By "reduced" it is meant reduced in relation to the numbers and/or concentrations of virus particles usually encountered in volumes used in the art as inocula for passage of virus in embryonated eggs, e.g. greater than 100 μl, usually 1 ml-2 ml.

Surprisingly, the invention provides the key to producing large quantities of cloned DI virus by being able to inoculate transfected cell culture medium into a multiplicity of embryonated eggs.

In another aspect, the method of the invention comprises the production of cloned DI influenza virus comprising (a) transfecting a cell with (i) a plasmid comprising an RNA segment of an influenza A virus that has a deletion therein, and (ii) plasmids which in combination provide RNA segments 1 to 8 of an infectious influenza A virus; (b) culturing the transfected cells for a period; (c) introducing at least a portion of transfected cell culture medium into at least 10 embryonated eggs, (d) incubating at least some of the eggs for a period; and (f) recovering virus material from at least one incubated egg.

The transfected cell culture medium will usually be in the range 0.1 μl-100 μl. In accordance with the invention, these volumes may be distributed amongst more than 10 embryonated eggs.

In preferred embodiments, the transfected cell culture medium is distributed amongst more than 10, preferably more than 25, optionally more than 50 eggs.

Up to 100, 150, 200, 250, 500, 1000, 2000, 5000 or more eggs may be inoculated with culture medium from a single transfected cell culture. The invention therefore opens up the field for producing large quantities of cloned DI influenza A virus for research and pharmaceutical/veterinary applications.

There may be a multiplicity of passages wherein after recovering DI virus material from eggs, culturing or passaging of the virus is repeated one or more times. The number of passages in eggs may be 3, 4 or 5 in order to generate the necessary yield of a cloned DI virus.

In the aforementioned methods where there is a step of reducing the number or concentration of virus particles prior to introducing virus material into eggs, this step may take place during two or more passages, optionally during every passage in embryonated eggs.

Aside from measurement of DI influenza A virus particles using a specific probe and/or primers, the amount of DI influenza A virus material in a culture medium or aliquot may be reflected by the number or concentration of total virus particles i.e. including any helper virus that is present.

Prior to a method of passaging virus in an aliquot known to contain or suspected of containing a cloned DI virus particle, the aliquot in question may be obtained previously by introducing starting material known or suspected of containing the cloned virus into an embryonated egg and incubating the egg for a period. Thus, in certain embodiments one does not need to have verified that a sample actually contains cloned DI influenza A virus; the passaging can be conducted blindly on a starting aliquot, the results determining the presence or absence of cloned DI influenza A virus in the inoculum.

The starting material referred to above is preferably obtained from a transfected cell culture. The cells are preferably Vero cells, more preferably HEK293T cells+MDCK cells.

In a method of passaging as described above, there may be one or more further passages, wherein recovered virus material is introduced into an embryonated egg and the egg incubated for a period followed by recovering further virus material from the egg.

One or more passages may be performed, wherein the inoculation and incubation of eggs is repeated one or more times.

In each of the methods described above, the concentration of virus particles may be reduced by dilution. The dilution may be at least $\frac{1}{2}$, preferably at least $\frac{1}{10}$, more preferably at least $\frac{1}{100}$, even more preferably at least $\frac{1}{1000}$. Other preferred dilutions can include, for example, $\frac{1}{3}$, $\frac{1}{4}$, $\frac{1}{5}$, $\frac{1}{6}$, $\frac{1}{7}$, $\frac{1}{8}$, $\frac{1}{9}$, $\frac{1}{11}$, $\frac{1}{12}$, $\frac{1}{13}$, $\frac{1}{14}$, $\frac{1}{15}$, $\frac{1}{20}$, $\frac{1}{25}$, $\frac{1}{30}$, $\frac{1}{35}$, $\frac{1}{40}$, $\frac{1}{50}$, $\frac{1}{60}$, $\frac{1}{70}$, $\frac{1}{80}$, $\frac{1}{90}$, $\frac{1}{200}$, $\frac{1}{300}$, $\frac{1}{400}$, $\frac{1}{500}$, $\frac{1}{600}$, $\frac{1}{700}$, $\frac{1}{800}$, $\frac{1}{900}$, $\frac{1}{2000}$, $\frac{1}{3000}$, $\frac{1}{4000}$, $\frac{1}{5000}$ or $\frac{1}{10,000}$.

Serial dilution may be carried out, e.g. a $\frac{1}{2}$ dilution followed by a $\frac{1}{10}$ dilution. Optionally, an aliquot of the first dilution may be taken prior to making the second dilution on that aliquot.

Alternatively, the number of virus particles may be reduced by dilution (as described above) followed by taking of at least a portion of the resulting diluted volume. This subsequent portion or aliquot may then be made up to a desired volume.

The dilution step may be used to achieve an exchange of buffer or alteration in solution components.

The infectivity of a preparation of virus particles produced by methods of the present invention can be ascertained as known in the art by using a plaque assay titration in MDCK cells under agar by standard procedures. A DI influenza A virus preparation of the invention preferably has fewer than $10^6$ plaque-forming units per HA unit, and may have as few as $10^5$, $10^4$, $10^3$, or $10^2$ plaque-forming units per HA unit.

The total amount of virus present in a DI virus preparation may additionally or independently be ascertained by using a standard haemagglutination (HA) test with chicken red blood cells (e.g. from Serotech or other commercial suppliers.) An aliquot of reduced concentration or number of DI virus particles in accordance with the invention may contain no more than about 400 HA units, preferably no more than about 100 HA units, more preferably no more than about 40 HA units. In other preferred embodiments an aliquot of DI influenza A virus particles employed in methods of the invention may have less than $10^2$ HA units, including less than 99, 98, 97, 96, 95, 90, 85, 80, 75, 70, 65, 60, 55, 50, 45, 40, 35, 30, 25, 20, 15, 10, 5 or 1 HA units. Aliquots of less than $10^1$, $10^2$, $10^3$ or $10^4$ HA units are also with the scope of the invention.

The cloned DI influenza A virus may be in the form of a preparation in which at least 75%, preferably at least 85%, more preferably at least 90%, even more preferably at least 95% of all virus particles in the preparation are genetically identical.

The inventor has found that cloned DI influenza A virus preparations made in accordance with the invention comprise up to 99.9% of virus with the deleted RNA segment, with the balance being made up of naturally occurring or wild-type (helper) virus. The preparations may comprise up to 99.8%, 99.7%. 99.6%, 99.5%, 99.4%. 99.3%, 99.2%, 99.1%, 99%, 95%, 90%, 85% or 80% cloned DI influenza A virus as a total of virus particles or genomes.

In preferred embodiments substantially all DI influenza A virus particles in the preparation are genetically identical, more preferably all DI virus particles are genetically identical.

The cloned DI influenza viruses of the invention preferably comprise 8 RNA segments with at least one of the segments having a deletion. The deletion may result in all or part of a gene encoding a surface antigen being deleted. In other aspects all or part of a polymerase gene may be deleted.

An aliquot of the virus preparation may be irradiated with UV light in order to inactivate at least a portion of infectious influenza A virus (i.e. helper virus) present in the aliquot. The amount of radiation required is expected to be proportional to the amount of infectious virus present in the aliquot. The UV targets RNA. Generally, a low dose of UV-irradiation may suffice. A UV lamp may be calibrated to achieve an inactivation of 1 $\log_{10}$ influenza virus infectivity per 4 seconds. UV-irradiation at 253.7 nm at approximately 10 cm and a sample depth of 2 mm with an 8 watt lamp is therefore carried out in the range 5 seconds to 3 minutes, preferably 10 seconds to 2 minutes, more preferably 30 seconds to 90 seconds. UV-irradiation preferably reduces infectivity of a DI influenza A virus preparation produced by methods of the invention down to levels less than $10^6$ PFU per HA units, preferably less than $10^5$, $10^4$, $10^3$ or $10^2$ PFU per HA unit.

Complete inactivation of all viral RNAs, including DI virus RNAs can be achieved by UV-irradiation for about 8 minutes, optionally 4 minutes.

The invention also provides a cloned DI influenza A virus for use as a medicament. The medicament is preferably an antiviral. The cloned DI influenza A virus has been found by the inventors to act as an antiviral agent. Moreover, the antiviral action is universal against all strains or sub-types of influenza A. The cloned DI influenza A virus that is administered may therefore be the same or a different sub-type to the influenza A virus acquired naturally by an individual. No adjuvant is needed because the antiviral effect of the medicament is not immunological in its basis, although the inventors have also found a secondary immunological response. The antiviral action is immediate and protective for the individual to which it is administered. Furthermore, no helper virus is needed to be administered. Administered cloned DI influenza A virus of the invention has a significant half-life in the body of the subject to which it is administered. Re-administration may take place up to a week, two week, three weeks or a month later in order to reinstate latent protective effect—the protective effect arising on infection of the individual with a naturally occurring influenza A virus of the same or a different sub-type.

Without wishing to be bound by any particular theory, the inventors believe that the presence of naturally occurring or wild type influenza A virus of any sub-type in the presence of cloned DI influenza A virus of the invention, results in a complementation of the defective segment such that the DI influenza virus can replicate at the expense of the natural or wild type virus in the host cells. A consequence is that the virulence of the natural or wild type virus is diminished allowing the body time to mount an effective immune response against the natural or wild-type virus. The cloned DI influenza A virus of the invention is not therefore a vaccine, but an interfering antiviral agent of universal application against influenza A sub-types.

In another aspect the invention includes the use of a cloned DI influenza A virus obtainable from any of the methods of the invention.

A cloned DI influenza A virus is used for the manufacture of an antiviral medicament for the prevention or treatment of the same or a different sub-type of influenza A in an individual.

In a further aspect, the invention includes the use of a cloned DI influenza A virus for the manufacture of a medicament for converting a virulent influenza A virus infection in an individual into an avirulent infection. The virulent strain of influenza A may be of any type, whether a human, animal or bird strain.

The invention advantageously provides for the use of a cloned DI influenza A virus for the manufacture of a medicament for providing immediate and non-immunological protective effect in an individual infected, or suspected of being infected with influenza A.

The inventors therefore provide antivirals based on naturally occurring defective interfering influenza RNAs that have the capability of protecting against any influenza A virus in any host. This so-called "protecting RNA" of known sequence is preferably encapsidated in virus particles, and is preferably delivered by intranasal administration to the cells of the respiratory tract that are naturally targeted by infectious influenza virus. A small dose of what the inventors call "protecting virus" (i.e. cloned DI virus) exerts strong prophylactic protection in mice against a lethal influenza infection, and gives therapeutic benefit. Protecting virus will provide an important option for combating influenza in people, particularly when the strain of virus is not known or is resistant to antiviral drugs.

The inventors have made virus preparations that contain a single dominant defective RNA. These cloned DI virus preparations, also called "protecting virus" preparations to distinguish them from the activity of 'interfering viruses' in cultured cells, have the ability to protect animals, including humans, from serious infection with influenza A viruses. In some embodiments, the inventors have made "protecting virus" with approximately 50-times more prophylactic activity against influenza A virus in mice compared with non-cloned DI virus. The "protecting virus" preparation provides therapeutic benefit.

The "protecting virus" RNA sequence advantageously allows for batch authenticity to be checked, specific activity to be measured, and mechanism of action of individual protecting RNAs to be determined.

A major advantage of protecting virus is that it is expected to work against any subtype or strain of influenza A virus. Viruses resistant to protecting virus are unlikely to arise as the active principle, protecting RNA, uses the same replication machinery as genomic RNA.

Consequently, an advantage is that an individual known or suspected of being infected with an influenza A virus can be treated for the infection, even if symptoms of infection have yet to be observed or infection diagnosed. The individual can be administered with the cloned DI influenza A medicament as soon as possible when an infection is suspected. Individuals can also be infected as soon as possible after having been in contact with other individuals of the same or different species and who are known or suspected to be infected with influenza A. Advantageously, protection is not believed to involve an immune response and is achieved on administration of the cloned DI virus medicament alone without the need for administration of helper virus. There is therefore no requirement to administer the cloned DI virus in advance of infection like a conventional vaccine (which relies on immune responses in order to generate a protective effect.

Medicaments of the invention may be administered to individuals on a precautionary basis. For example, health workers and people working with animals or birds (dead or alive) and who are at risk of exposure to influenza A virus.

In yet a further aspect, the invention includes the use of a cloned DI influenza A virus for the manufacture of a medicament for vaccinating an individual against influenza A, wherein the medicament further comprises at least one live strain of influenza A, and the medicament is suitable for separate, simultaneous or sequential administration of the DI influenza A virus with the live (helper) strain. The helper strain may be an influenza A virus of any type, whether from humans, animals or birds.

The inventor has disclosed that a cloned DI influenza A virus is capable of acting together with a helper virus as a vaccine against the particular strain of influenza A virus. At the same time, the administration of cloned DI influenza A virus also has an antiviral effect.

Consequently, the invention provides a method of vaccinating an individual against a strain of influenza A virus and simultaneously treating the individual against an infection caused by any strain of influenza A virus, comprising administering an effective amount of a cloned DI virus and a live influenza A virus.

Also, the invention provides the use of a cloned DI influenza A virus for the manufacture of a medicament further comprising a live influenza A virus strain, wherein the medicament is a vaccine against the influenza virus strain and an antiviral agent against any strain of influenza virus.

In preferred embodiments, the medicament is administered intranasally. Other routes of administration may include mucosal, pulmonary and oral cavity. Other routes include gastro-intestinal via oral administration.

The individual to which the medicament may be administered may be an animal or human, preferably wherein the animal is selected from a pig, horse, dog, cat or bird (wild or domesticated).

In the case of birds, whether wild or domestic, the medicament may be administered conveniently via the oral tract, e.g. by incorporating the medicament in drinking water or in food. In the case of bird species, preferred domesticated species include, for example, duck, goose, turkey, or hen e.g. broiler chicken.

The medicament protects against any heterologous influenza A virus, not just the type homologous to the cloned DI virus.

The dosage regime may consist of a single dose of medicament. Advantageously, the administration of the dose may be timed to allow up to about 8 weeks prior to possible infection with an influenza A virus. The period of prophylaxis provided by the invention may be in the range 0-6 weeks, 0-5 weeks, 0-4 weeks, 0-3 weeks, 0-2 weeks or 0-1 week. An extended period of up to 12 weeks or longer is possible.

In a medicament which requires the simultaneous, separate or sequential administration of at least one live strain of influenza A, the strain may be any naturally occurring influenza A strain. For example, the live strain of influenza A may be selected from H1N1, H2N2, H3N2, H3N8 or H5N1.

The amount of cloned DI influenza A virus in the medicament is in the range per dose of 0.05-500 HAU, preferably a range selected from 0.1-100, 0.5-50 or 1-10 HAU. Other possible ranges include 0.05-10 HAU, 0.1-50 HAU and 1-100 HAU. However, because of the presence of helper virus, HAU values measured represent the sum of HA units for both helper and cloned DI virus.

The amount of cloned DI influenza A virus in the medicament can be measured by quantitative RT-PCR. Probes and/or primers specific for the deleted RNA segment are employed.

The amount of cloned DI influenza A virus in the medicament may be of the order (per dose) of 1 ng-1 μg of virus (measured in terms of total virus protein). The amount of DI virus may be in the range 0.05 μg-0.5 μg, optionally 0.1 μg-0.5 μg. Preferred embodiments include 0.01-0.1 μg or 0.01-1 μg of virus protein, more preferably 10 ng, 100 ng or 1 μg virus protein. The amount of virus protein includes both helper virus and cloned DI virus.

The amount of cloned DI influenza A virus, whether measured in terms of HAU or μg virus protein per dose, may be varied according to the subject. For example, a horse may require 4× the human dose, whereas a bird may require ⅒ of the human dose.

The defective RNA in a cloned DI influenza A virus has at least one deletion compared with the genomic segment from which it derived, although a multiplicity of deleted portions of segment 1 may occur. The deletions may be separated by a multiplicity of contiguous nucleotides.

The 5' and 3' ends of the genomic segment including the deletion are preferably intact. In a more preferred embodiment the segment is segment 1.

The effect of deletion is that the 5' end of the segment of virion RNA has at least 150, 200 or 220 nucleotides. Preferably the 5' end of the segment has a number of nucleotides in the range 150-500, more preferably 150-250, or 150-220.

In terms of the 3' end, the remaining (undeleted) portions comprise at least 20, 50, 100, 200, 300, 400 or 500 nucleotides. The 3' end of segment 1 may have a number of (undeleted) nucleotides in the range 20-600, 30-550, 40-500, 50-450, 60-400 or 75-250.

The segment deletion may be at least 50% of the nucleotides, preferably at least 75%, more preferably at least 80% of the nucleotides. In order for an effective deletion in the RNA segment, at least one nucleotide may be deleted. In more preferred embodiments, the deletions may consist of at least 3, 5, 10, 15, 20, 25, 50, 75, 100, 150, 200, 250, 300, 400, 500, 750, 1000, 1500, 3000 or 5000 nucleotides, preferably contiguous nucleotides. A multiplicity of deletions is possible within the same RNA segment.

The nucleotide sequence of genomic segment 1 of a cloned DI influenza A virus according to the invention may comprise:

(a) a sequence selected from SEQ ID NO:1 or SEQ ID NO:2, or: (b) a nucleic acid sequence of at least 75% identity with SEQ ID NO:1 or SEQ ID NO:2;

(c) the complement of a sequence which hybridizes with (a) or (b) above under stringent conditions.

Preferably the sequence of the genomic segment 1 of the cloned DI influenza A virus has at least 80%, preferably at least 90%, more preferably at least 95%, even more preferably 99% identity with SEQ ID NO: 1.

In another preferred embodiment the sequence has greater than 96% identity with SEQ ID NO: 1.

The nucleotide sequence of genomic segment 1 may comprise an insertion of one or more nucleotides at one or more positions in the nucleotide sequence.

In a preferred embodiment, the nucleotide sequence of genomic segment 1 is SEQ ID NO:1.

The invention therefore provides a pharmaceutical composition comprising a cloned DI influenza virus A as hereinbefore described.

Pharmaceutical compositions of the present invention, suitable for administration, comprise the DI influenza A virus, optionally helper virus, in sterile aqueous or non-aqueous solutions, suspensions, and emulsions. The compositions may further comprise auxiliary agents or excipients, as known in the art, see, e.g., Berkow et al., The Merck Manual, 16$^{th}$ edition Merck & Co., Rahman, N.J. (1992), Avery's Drug Treatment: Principles and Practice of Clinical Pharmacology and Therapeutics, 3$^{rd}$ edition, ADIS Press, Ltd., Williams and Wilkins, Baltimore, Md. (1987) & Osol (ed.), Remington's Pharmaceutical Sciences, Mack Publishing Co., Easton, Pa. 1324-1341 (1980). The composition of the invention is preferably presented in the form of individual doses (unit doses).

Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, e.g. purified water. As well as inert diluents, exemplary compositions may also include adjuvants, wetting agents, emulsifying and suspending agents, or sweetening, flavoring, or perfuming agents.

When a composition or medicament of the present invention is used for administration to an individual, it may further comprise salts, buffers, or other substances which are desirable for improving the efficacy of the composition.

Preferred compositions or medicaments are for mucosal delivery. Of the various mucosal delivery options available, the intranasal route is the most practical as it offers easy access with relatively simple devices that have already been mass produced. The composition of the invention is thus preferably adapted for and/or packaged for intranasal administration, such as by nasal spray, nasal drops, gel or powder (see Almeida & Alpar (1996) *J. Drug Targeting* & Agarwal & Mishra (1999) *Indian J. Exp. Biol.* 37:6-16.)

Other possible routes for mucosal delivery include oral, intragastric, pulmonary and intestinal. The composition of the invention may be adapted for and/or packaged for mucosal administration (e.g. see Walker (1994) *Vaccine* 12:387-400, Clements (1997) *Nature Biotech.* 15:622-623 & McGhee et al. (1992) *Vaccine* 10:75-88). For oral administration tablets or capsules (optionally enteric-coated), may be provided. Optionally, liquid, transgenic plant material, drops, inhaler, aerosol, enteric coating, suppository, pessary, etc. (see Michetti (1998) *J. Gastroenterol.* [Suppl X]: 66-68 and chapter 17 of *Vaccine design: the subunit and adjuvant approach*, eds. Powell & Newman, Plenum Press 1995).

Whatever the route of delivery, compositions or medicaments of the invention are preferably in unit dose form. Effective doses can be routinely established. For example, a typical human dose of the composition for injection or for intranasal use has a volume between 0.1-0.5 ml e.g. two 100 µl sprays, one per nostril.

Compositions of the invention are preferably sterile and preferably not pyrogenic. At higher concentrations, DI influenza A virus composition may be pyrogenic or exhibit residual pyrogenic activity. The are preferably buffered e.g. at between pH 6.5 and pH 8, generally around pH 7.

An advantageous form of nasal administration is described in WO2006/041819 (Medimmune).

Consequently, the invention includes a method of preventing or treating influenza A in a subject comprising administering an effective amount of a cloned DI influenza A virus particle.

The cloned DI influenza A virus particle preferably has antiviral effect in the subject. In other aspects, the administration of cloned DI influenza A virus preferably provides immediate protective effect against an acquired influenza A infection.

Additionally or alternatively, the influenza A virus infecting the subject is the same or a different sub-type from the administered DI influenza A virus particle.

The invention also includes a method of converting a virulent influenza A virus infecting a subject into an avirulent virus infection, comprising administering to the subject an effective amount of a cloned DI influenza A virus.

The invention further provides a method of vaccinating a subject against influenza A virus comprising administering to the subject an effective amount of a cloned DI influenza A virus and an infecting amount of a live virus of at least one strain of influenza A. The live virus acts as a helper virus.

The cloned DI influenza A virus particle and the live virus may be administered separately, simultaneously or sequentially.

The invention further provides a method of converting a virulent influenza A virus infecting a subject into an avirulent virus infection that vaccinates the subject against the infecting virus, comprising administering to the subject a cloned DI influenza A virus.

The subject may, or may be suspected of being, infected with an influenza A virus. In cases of actual or even suspected infection, cloned DI virus may be administered as soon as possible, within 48 hours, preferably within 24 hours of the individual being infected, or being suspected of being infected. Similarly, individuals can be administered the cloned DI virus as a precautionary measure if they are shortly to be exposed to influenza A virus, whether infected humans, animals or birds. Persons having to deal with animal or bird carcasses or with human corpses known or suspected of being infected with influenza A can be administered the cloned DI virus of the invention. Such persons can be administered the medicament of the invention on a precautionary basis immediately prior to risk of influenza A virus exposure.

In each of the methods of the invention described above, the cloned DI virus is administered in sufficient amount. The helper virus may be of any influenza A strain, whether from humans or other animals, including birds.

In another aspect the invention provides a nucleic acid molecule comprising:
(a) SEQ ID NO:1 or SEQ ID NO:2; or
(b) a nucleotide sequence having greater than 96% identity with SEQ ID NO:1 or SEQ ID NO:2; or
(c) a nucleotide sequence that hybridizes with SEQ ID NO:1 or SEQ ID NO:2 under stringent conditions; or
(d) a nucleotide sequence complementary to any of sequences (a), (b) or (c).

The nucleotide sequence may have greater than 96.5, 97, 97.5, 98, 98.5, 99, 99.5, 99.6, 99.7, 99.8 or 99.9% identity with SEQ ID NO:1.

The invention also includes compositions comprising a nucleic acid molecule as defined above.

The nucleic acid is preferably RNA, although DNA may be employed during genetic manipulation procedures.

Also provided by the invention is a vector or plasmid comprising a nucleic acid as described herein. Vectors may include a promoter operably linked to the nucleic acid of the invention, optionally a transcription termination sequence. The nucleic acid of the invention may be in a sense or an antisense direction to the promoter.

Nucleic acids of the invention incorporated into influenza virus A particles have been found advantageously to show far greater protective effective against influenza A than other cloned DI viruses, for example 317/Vic or 220/PR8. (See Duhaut & Dimmock, 2003, J. Virol. Methods 108:75 82). Preferred cloned DI viruses of the invention show at least 10-fold, more preferably at least 100-fold greater protective activity against influenza A. In other preferred embodiments the protection is in the range 8 to 500-fold, more preferably 50 to 250-fold protection.

Protective effect may be established in vivo in suitable animals, e.g. mice, ferrets, from lethal challenge with any infectious influenza A virus.

The protective effect may be the prophylactic effect of the cloned DI virus of the invention when administered alone (without infectious helper virus) or it may include co-administration with a helper virus (which may be homologous/heterologous), possibly also of the same strain as the challenge virus The invention further includes a primer or probe nucleic acid molecule comprising at least a portion of a nucleic acid sequence as described herein.

Known methods of vaccinating against influenza depend on stimulating the body's immune system, so that white blood cells produce antibodies that attach to the surface of the microbe and start the process of killing it. This works well for many diseases, such as smallpox, polio and measles, but is much less effective with influenza, as the coat of the flu virus is continually changing. Vaccination against one strain of 'flu, for instance H3N2, is totally ineffective against another, such as H5N1. This is especially problematic when a new pandemic strain emerges, as all existing vaccines are likely to be totally ineffective.

In a public health and medical context, DI virus of the present invention can also be known as a "protecting virus". The protecting virus protects animals against various strains of flu, and offers protection against the full range of influenza A infections, including H5N1 and any new pandemic or epidemic strains infecting humans. The protecting virus provides instant protection, and completely prevents 'flu symptoms developing by slowing influenza infection rates to such an extent that the harmful infection becomes a vaccine against that very form of influenza. It can also counter an actual infection and offer protection if given up to 24 hours and longer after first infection.

In preferred embodiments of the invention, the specific deletion of about 80% of the RNA of one of the 8 RNA strands of the virus confers a protective activity on the virus when administered the humans, animals or birds. "Protecting virus" offers instant flu protection and converts flu infections into their own vaccines.

The deletion makes the protecting virus harmless and prevents it from reproducing by itself within a cell, so that it cannot spread like a normal influenza virus. However, if it is joined in the cell by another influenza virus, it retains its harmless nature but starts to reproduce—and at a much faster rate than the new influenza virus. This fast reproduction rate—spurred by the new 'flu infection—means that the new invading influenza is effectively crowded out by the "protecting virus". This vastly slows the progress of the new infection, prevents 'flu symptoms, and gives the body time to develop an immune response to the harmful new invader. In effect the protecting virus converts the virulent virus into a harmless live vaccine.

The "protecting virus" has the same beneficial effect, whatever strain of influenza is infecting an individual. Experimental results demonstrate this advantage. This is because the coat of the virus is irrelevant to the protection process—the effect works on the virus genes inside the cell. The protecting virus therefore represents a highly effective tool when combating the spread of any new strain of virus, as well existing strains. One could give it as a preventive measure without the need to tailor it to a particular 'flu strain or mutation. This has obvious benefits when dealing with the sudden outbreak of a major epidemic, as one would not need to know the exact make up of the new strain before deploying the protecting virus making it much more useful than vaccines, which are effective only against particular existing strains of virus.

In addition it protects instantly, whereas protection generated by conventional 'flu vaccination takes 2-3 weeks to become fully effective. Experiments show that a single dose of protecting virus can be given 6 weeks before an infection with 'flu virus and be effective. This has substantial advantage over anti-viral drugs that only give less than 24-hours of protection. Another advantage is that influenza virus does not appear to become resistant to "protecting virus".

"Protecting virus" also protects when given up to 24 hours after infection and beyond. It is thus able to counter an actual infection. It can therefore also be used as a treatment for family and other direct contacts of infected individuals.

"Protecting virus" is easy to administer as it targets the same cells as any other 'flu virus and uses the same method to enter the cell. A drop of saline containing the protecting virus can simply be squirted up the nose. Aerosol administration, used already for some vaccines, offers another simple route of administration.

The protecting virus provides a useful treatment for domestic animals. Ducks get a gut infection and chickens a combined gut and respiratory infection. The protecting virus can simply be delivered to them in their drinking water. One dose can provide a chicken, for example, with at least a week of protection.

'Flu is a major problem in the horse racing industry and in domestic horses. It also has very recently become a problem in domestic dogs in the USA and domestic cats are susceptible to H5N1 virus.

Intranasally administered cloned DI influenza viruses (i.e. "protecting viruses") give excellent prophylactic activity against a strong infectious virus challenge in both mouse and ferret models—the latter mimicking closely human disease. So far, the best DI virus (244/PR8) is approximately 50-fold more active than any non-cloned DI virus (Noble et al, 2004 Vaccine 22: 3018-3025), and also protects mice for far longer than non-cloned DI virus. Further, only cloned and thereby DI virus has therapeutic activity—probably a function of its overall higher activity.

Different cloned DI viruses vary in the magnitude of their antiviral activity when normalized to total HAU.

Defective RNAs or the HA gene present in naturally non-replicating or UV-irradiated infectious virus persists in cultured cells (Cane et al 1987, Virology 159: 259-264; Cane & Dimmock, 1990 Virology 175: 385-390), but the persistence of cloned DI "protecting" RNA in vivo was unexpected. Influenza A virus RNAs were not generally thought to persist in immunocompetent animals.

As a non-cloned DI virus population contains a rich assortment of defective RNAs, it has not been possible to determine a molecular mode of action. Without wishing to be bound by any particular theory, the inventors believe that one possibility is that the copying of an RNA genome is proportional to its size, so that a protecting RNA that is 5 times smaller is replicated 5-times faster. Thus, starting from equal numbers of defective and infectious genomes in a cell, over 90 and 99% of genomes would be defective after 4 and 6 rounds of replication respectively. Under these conditions, assuming that influenza RNA packaging is an organized process and that the defective RNA and its full-length counterpart are packaged with equal efficiency, the majority of progeny particles will contain a defective RNA and be non-infectious. In addition to this reduction in infectious progeny, defective virions would transmit protecting RNA to neighboring cells and make them resistant to infection. Defective RNA may also compete with its non-defective counterpart for limiting amounts of viral or cell constituents, induce alpha/beta interferon, or form siRNAs from defective RNA—although the latter is only known to occur in plant systems. Indeed, such mechanisms might work in concert.

Protecting concentrations of cloned and non-cloned protecting viruses attenuate the virulent virus infection in mice and ferrets. There is no clinical disease, but there is enough virulent virus antigen produced to stimulate an adaptive immune response that renders these animals immune to re-infection with homologous virus. Counter-intuitively, immunity was weakest after treatment with the highest concentration of protecting virus, presumably because antigen formation is suppressed to an almost sub-immunogenic level.

Cloned DI "protecting" virus potentially offers a number of advantages over vaccines or existing drugs in combatting pandemic influenza. The problem of influenza vaccines is their exquisite specificity for the virus strain of the day. When a new virus appears, it can take several months to a year to select a new strain, produce and test a vaccine, and distribute and administer it to a significant section of the world's population. Full vaccine-induced immunity takes approximately 3 weeks to mature, and the elderly may be incapable of mounting an effective immune response. In contrast, protecting virus exerts its full effect immediately, and should be active against any strain of influenza A. Its activity resides in the viral genome rather than that of the host, so protection should also be effective in the elderly.

A major limitation of anti-viral drugs is the rapidity with which resistance occurs, and human influenza isolates resistant to Tamiflu have already been isolated. However, protecting RNAs are dependent on the highly conserved replication machinery of normal virus, so resistance is unlikely to arise.

Subsequent doses of protecting RNA may be given using antigenically different helper viruses. It will also be necessary to select a helper virus to which most of the human population has no immunity and which is avirulent—such as the A/PR8 (H1N1) virus used by the inventors.

The invention will now be described in detail with reference to specific examples and to drawings in which:

BRIEF DESCRIPTION OF THE DRAWINGS

FIG. 1 shows a nucleotide sequence of 244/151PR8 (SEQ ID NO:1) being an example of a DI influenza A virus of the invention. The sequence is that of the virion-sense RNA.

FIG. 2 shows a nucleotide sequence of 244/151PR8 (SEQ ID NO:2) being an example of a preferred DI influenza A virus of the invention. The sequence is that of the virion-sense RNA.

DETAILED DESCRIPTION OF THE INVENTION

Figure 3:
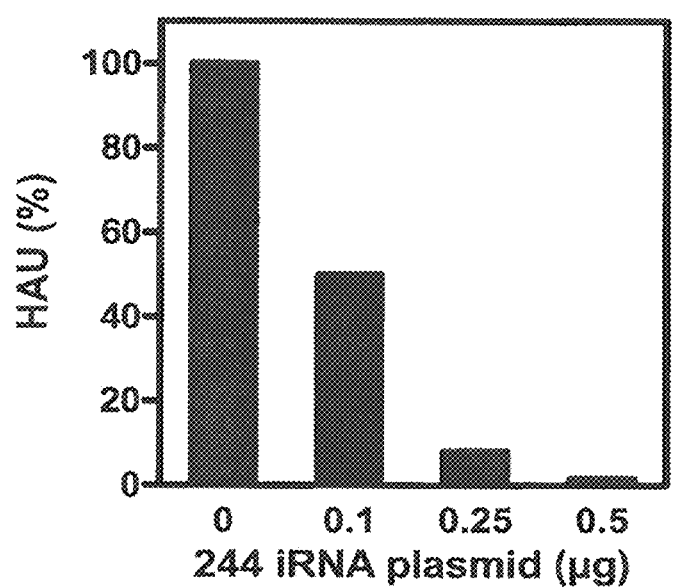
FIG. 3 shows how transfection of 293T cells with the 244 protecting influenza RNA expression plasmid and plasmids expressing infectious A/WSN inhibits the production of A/WSN virus.

Most DI influenza A viruses have a single internal deletion. In terms of nomenclature, an example of the cloned DI virus RNA, described here is:

RNA1__244/151/395_A/PR/8/34(H1N1)×A/PR/8/34 (H1N1).

Thus:
(a) The initial term refers to the fact that it is derived from RNA segment 1 of A/PR8/34 (H1N1) virus.
(b) The next term indicates that it comprises 244 nt from the 5' end and 151 nt from the 3' end of the RNA 1 as found in the virion, and that these are linked together to form a continuous new RNA molecule of 395 nt.
(c) The end term refers to the helper virus, A/PR8/34 virus.
(d) Its abbreviated name is 244/151PR8.

Where not otherwise apparent to a reader of average skill in this art, the specific examples of experiments described below employed the following methods and procedures:
Preparation of Cloned DI Virus Methods used in the specific examples are described below and subject to variation are also to be found in the materials and methods described in Duhaut & Dimmock (2003) supra.

HEK293T cells were transfected using known methods with the set of plasmids that is necessary for making infectious A/PR8/34 virus (H1N1).

The transfected cells were then co-cultured with MDCK cells to amplify infectious virus. Tissue culture fluid containing the infectious virus and any DI virus present was harvested and, after debris was removed by low-speed centrifugation, was stored at −70° C. The presence of virus was shown by agglutination of chicken red blood cells (see below). The titre of virus is recorded as haemagglutinating units (HAU) of virus per ml.

Tissue culture fluid (500 μl) was then injected into the allantoic cavity of 10-day-old embryonated hens' eggs in order to boost the concentration of infectious virus and putative DI virus present. Eggs were incubated for 1 day at 33° C., and then chilled at 4° C. overnight to kill the embryo. Allantoic fluids were then harvested from the eggs by standard methods.

The amount of virus was determined by haemagglutination. Virus-containing allantoic fluids were clarified by low-speed centrifugation, and purified (see below). Virus was aliquotted and stored in liquid nitrogen or at −70° C. at a concentration of $2 \times 10^5$ HAU/ml.

Preliminary tests (see below) showed that this preparation protected mice from a lethal intranasal challenge of A/WSN influenza virus and therefore that DI RNA had been generated.

RT-PCR with segment 1 specific primers (see below) showed that RNA 1 of A/PR8/34 had given rise to a truncated RNA. Subsequent sequencing showed that there was a major truncated RNA species present of 395 nucleotides, and that it was homologous with RNA 1 of A/PR8/34. This RNA is termed 244/151PR8.

Viruses containing cloned segment 1 defective RNAs 220 (H3N8) and 317 (H7N7) (Duhaut, S. D. & Dimmock, N. J. 1998, *Virology* 248: 241-253) were created by cotransfection of 293T cells with viral and defective RNA plasmids, and cocultivation with MDCK cells. A third defined defective RNA (244), also segment 1, was formed spontaneously following transfection of A/PR8 virus plasmids (see Table 1a below).

Table 1a below shows the derivation and nomenclature of protecting influenza RNAs and their helper viruses.

TABLE 1a

| Abbreviation[a] | Defective RNA[b] | Helper virus |
|---|---|---|
| 220/PR8 | RNA1__220/445__A/equine/Newmarket/7339/79 (H3N8) | A/PR/8/34 (H1N1) |
| 220/Vic | As above | A/Victoria/3/75 (H3N2) |
| 317/Vic | RNA1__317/585__A/chicken/Dobson/27 (H7N7) | A/Victoria/3/75 (H3N2) |
| 244/PR8 | RNA1__244/395__A/PR/8/34 (H1N1) | A/PR/8/34 (H1N1) |
| 244/WSN | As above | A/WS/33(N) (H1N1) |

[a]220, protecting RNA; PR8, helper virus.
[b]Denotes from left to right: segment of origin of defective viral RNA, breakpoint residue in the minus-sense RNA, total number of nucleotides, virus of origin.

Removal of Helper Virus Infectivity from the DI Virus Preparation

By definition, a stock of DI virus contains infectious helper virus. The infectivity must be removed before the animal to be protected is inoculated. Thus, the virus is placed in a plastic dish so that it from a layer of approximately 1-2 mm and is irradiated at room temperature with a critical dose (20 seconds) of UV light. UV-irradiation targets nucleic acids in proportion to size, and rapidly inactivates the infectivity of helper virus. DI virus RNA (395 nt) and its activity is not significantly affected as it has a 34-fold smaller UV target size than that of the infectious genome (13,600 nt). The dose of UV required was determined by measuring the rate of inactivation of infectivity of A/PR8/34 virus under the same conditions.

Following UV inactivation of helper virus, inoculation of MDCK cells, embryonated eggs, and mice (intranasally, followed by culture of homogenized lungs in embryonated eggs) showed no residual infectivity (data not shown). Prolonged UV irradiation destroyed the mouse-protecting activity of defective virus (see below).

Purification of DI Virus

Debris present in allantoic fluid was removed by low-speed centrifugation. The supernatant was then centrifuged at high speed over an approximately 25 mm spacer layer of 10% sucrose. Low density impurities collected on the sucrose and virus pelletted to the bottom of the centrifuge tube. After allowing the pellet to soften overnight, virus was resuspended at $2\times10^5$ HAU/ml in PBS or PBS containing 0.1% w/v bovine serum albumen. This was then aliquoted, and stored frozen in liquid nitrogen or at $-70°$ C. All procedures were carried out at $4°$ C.

Authenticity of Passaged Defective Virus

The presence of the expected defective RNA in the final purified virus stock (after 1 cell and 2 egg passages) was confirmed by RT-PCR using a terminal primer and a primer specific to the unique junction sequence formed after the central deletion takes place. RNAs were finally authenticated by sequencing. Further analysis of the 244/PR8 defective virus with segment-specific primers showed that the 244 was the major RNA present.

Assay of Influenza Virus by Haemagglutination

This assay relies of the fact that the major protein present on the surface of the virus, the haemagglutinin, binds to viral receptors on the chicken red blood cell and many viruses can link the cells together and cause them to agglutinate. The assay is independent of infectivity and measures both infectious and non-infectious influenza virus. Virus is serially 2-fold diluted in wells in a plastic assay tray in saline diluent, and a tenth dilution of chicken red blood cells added. After thorough mixing, red cells are allowed to settle. When no virus is present, red cells settle to form a small button at the bottom of the well; when virus is present red cells are agglutinated and form a thin even layer over the bottom of the well. The titre of the virus is determined by interpolation of the dilution that gives 50% agglutination. The advantage of the assay is its speed—red cells settle in about 45 minutes. The assay is usually carried out at room temperature.

Protection of Mice from Influenza with DI RNA

Mice (strain C3H/He-mg: H-$2^k$) were inoculated intranasally with DI virus, which had been UV-irradiated for 20 seconds to remove the infectivity of infectious helper virus. The DI virus preparation was not infectious when inoculated neat into embryonated chicken's eggs, and had no observable affect on mice. Mice were 4 to 5 weeks-old and weighed 16-20 g. Both sexes were used but housed separately. Control groups were matched for sex. Mice were lightly anaesthetized with ether, and a 40 µl of DI virus divided between the two nares.

Any immune system-stimulating or receptor-blocking effects of the DI virus were controlled for by using DI virus that had been given prolonged UV irradiation of 8 min. This inactivates the DI activity, but does not affect activities of the haemagglutinin or neuraminidase proteins present on the surface of the virus.

Two infectious challenge viruses were used. These were titrated in mice to determine a dose for each that caused comparable respiratory disease.

Mouse inocula usually comprised:
  (a) Active, non-infectious DI virus, sometimes containing a defined dose of infectious challenge influenza virus.
  (b) UV-killed DI virus containing the same dose of infectious influenza virus.
  (c) Active DI virus alone
  (d) Diluent.

Morbidity was assessed according to loss of weight, and by clinical criteria. Weight loss can be severe and amount to over 25% of the initial weight. Disease progression is defined as:
  (a) Healthy mouse
  (b) Clinical signs of malaise, including slight piloerection, slightly changed gait, and increased ambulation
  (c) Clinical signs of strong piloerection, constricted abdomen, changed gait, periods of inactivity, increased breathing rate, and sometimes râles
  (d) Clinical signs as above, but enhanced; also showing little activity, and becoming moribund. Such mice are killed when it is clear that they would not survive
  (e) Death.

All viruses tested cause similar clinical disease. In addition at autopsy all viruses cause similar lung consolidation.

While detection of any one of the clinical signs is an objective observation, the degree to which it is expressed is subjective. However with experience even a slightly sick mouse is easy to spot. The time scale of lethal influenza depends on virus dose but typically clinical signs commence within 3-5 days and proceed to death in another 2-4 days. The clinical course of non-lethal disease will be longer. There are differences in virulence between influenza virus strains (i.e. the amount of infectious virus required to cause disease), but they all give a similar clinical manifestation. Inbred mouse strains differ in susceptibility (i.e. the amount of infectious virus required to cause disease), but on limited data the disease pattern is similar. C3H/He-mg mice are a preferred susceptible strain that give reproducible disease in most inoculated animals.

Mice are also weighed as an objective measure of disease. Mice are used at 4-5 weeks of age (16-20 g) when they are still gaining weight. A mouse gains about 500 mg/day. As infection advances mice cease to gain weight and then start to lose weight. This occurs about one day before they show signs of sickness (as in 1b above). Mice are weighed as a group which usually comprises 5 mice or more. Thus a loss of around 2 g (400 mg/mouse) is readily detected. Mice can lose up to 25% of total body weight before death/culling i.e. a 20 g mouse would lose 5 g.

RT-PCR Protocol

RNA was extracted from virus with Trizol reagent (Invitrogen), and dissolved in 100 µl water. Alternatively RNA was extracted from the lungs of one mouse by grinding with sterile sand in 4 ml Trizol. Aliquots of 5 µl total RNA (or RNA from 200 µl virus) were reverse transcribed in 20 µl reactions for 1 hr at $42°$ C., using a generic type A influenza RNA 1 specific primer (RNA1F:

5'AGCGAAAGCAGGTCAAATATA3'), complementary to the 3' terminus of the vRNA. RNA 1 encodes the PB2 protein component of the viral replicase. Aliquots (1.5 µl) of the reverse transcription reaction were then amplified by PCR using Taq DNA polymerase (MBI Fermentas or New England Biolabs) and generic primers specific for RNA 1 of influenza A virus, RNA1F and RNA1R (5'AGTAGAAACAAGGTCGTTTTTA3', complementary to the 3' terminus of the cRNA or a primer specific for the junction sequence in the 244 iRNA, 244J (5'ATCCCCT-CAGTCTTCTCCTG3') in a 25 μl reaction volume. RNA1F has a single mismatch to the published PR8 sequence whereas RNA1R is identical to the published PR8 sequence. PCR consisted of 30 cycles of 94° C. for 20 s, 50° C. for 30 s and 72° C. for 30 s. Aliquots of 10 μl were analysed by agarose gel electrophoresis.

Verification that Mouse-Protecting Activity Resides in RNA 244

As trace amounts of other defective RNAs were present, it was important to verify that the antiviral activity of 244/PR8 in mice resided in RNA 244, rather than a combination of 244 and another defective RNA. To this end, cloned 244 RNA was transfected into an expression plasmid together with plasmids encoding infectious A/WSN. In a parallel titration, the resulting defective 244/WSN virus had the same protecting activity as 244/PR8 (complete protection with 100 ng per mouse and at least 10-fold higher than other defective viruses—see Table 15 below) confirming that RNA 244 was responsible for prophylaxis (data not shown). This also demonstrates the ease with which a defective RNA can be transferred to a new helper virus.

Defined Defective Viruses Prophylactically Protect Mice Against Infectious Influenza Virus Mice were inoculated intranasally with either defective virus or with defective virus that had been UV irradiated to destroy its potential protecting activity. The latter retains full H and N activities and serves as a control for immunogenicity and cell receptor blockade. In the first experiments, mice were inoculated simultaneously with a single dose of protecting virus (400 HAU) and mouse-pathogenic infectious A/WSN.

Figure 4:
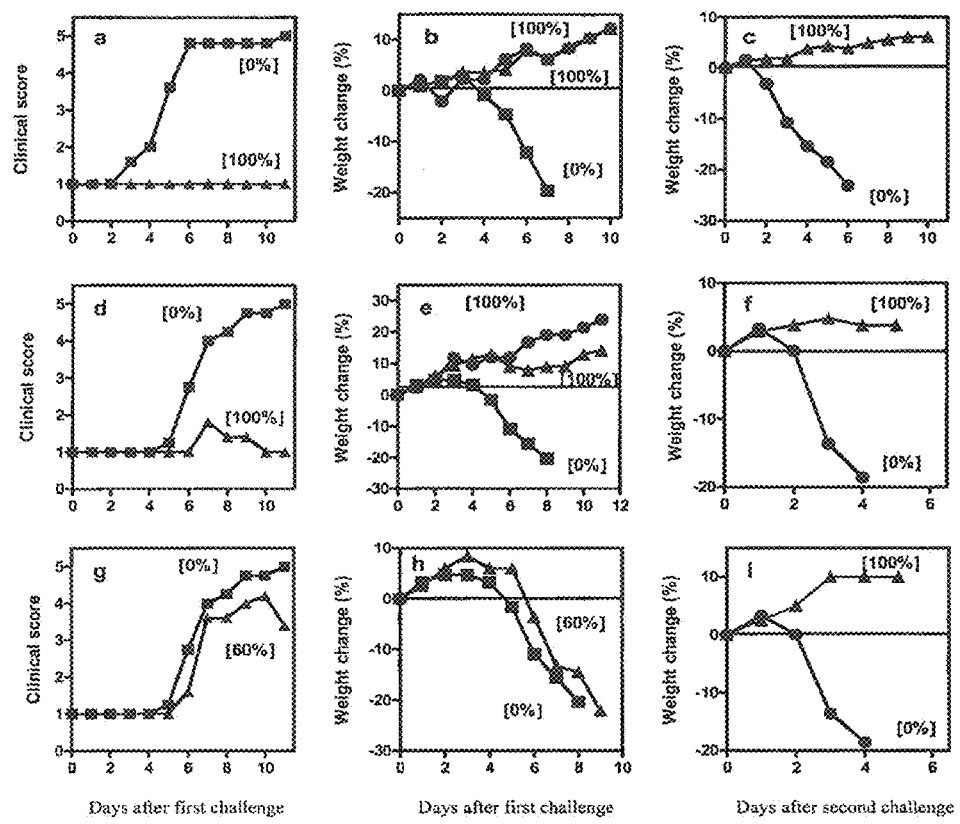
FIG. 4 shows prophylactic activity mediated by protecting virus 244/PR8 in mice against infectious A/WSN, as monitored by clinical disease and body weight change.

FIG. 4 shows prophylactic activity mediated by protecting virus 244/PR8 in mice against infectious A/WSN, as monitored by clinical disease and body weight change. Mice received 400 (a, b, c), 40 (d, e, f), and 4 HAU (g, h, i) of 244/PR8 protecting virus simultaneously with 10 $LD_{50}$ A/WSN. The figure shows clinical scores (a, d, g) and weight changes (b, e, h). Percentage survival is in parenthesis. Symbols denote the inocula given in panels a, d, g: ■, inactivated protecting virus+10 $LD_{50}$ A/WSN; ▲, protecting virus+10 $LD_{50}$ A/WSN; ●, diluent. Panels c, f, i show the result of challenging survivors with 10,000 $LD_{50}$ A/WSN, 3 weeks after the first infection. As the highest dose of protecting virus gives no protection against this high dose of A/WSN (not shown), this test the development of adaptive immunity.

Mice that received UV-inactivated protecting virus plus A/WSN suffered weight loss and clinical disease, and all died (FIG. 4a, b). This was identical to the disease in mice receiving infectious virus alone (data not shown). In comparison, mice receiving protecting virus plus A/WSN continued to gain weight as did the mock-infected control animals and showed no sign of disease (FIG. 4a, b). A 10-fold dilution of protecting virus (to 40 HAU/mouse) kept major clinical disease and death at bay, although there was a slight, transient weight loss and some malaise, which resolved by day 10 (FIG. 4d, e). Finally, 4 HAU of protecting virus per mouse slowed the onset of clinical signs and weight loss and increased survival to from 0 to 60% (FIG. 4g, h).

The same minimum dose (40 HAU/mouse) of 244/PR8 gave solid protection from infectious virus challenge with 4 independent preparations, attesting to the reproducibility of production and action of protecting virus. This was equivalent to 100 ng of virus protein or 400×10⁶ virus particles per mouse. All preparations also gave significant protection with 10 ng of protecting virus. Three other protecting viruses containing one or other of 2 different defined segment 1 protecting RNAs, which were produced, HAU normalized, and tested in exactly the same way, were 10 to 100-fold less active than 244/PR8 (see Table 15 below). These had the same relative ability to protect against A/PR8, showing that the differences were not challenge virus-specific (data not shown). RT-PCR quantitation of the number of protecting RNA molecules in each preparation is needed to determine if there is indeed variation in the intrinsic activity of protecting RNAs, or in the efficiency with which they are replicated or packaged by particular helper viruses. The 10-fold variation in protecting activity of RNA 220 in the context of A/PR8 or A/Vic helper viruses may indicate the importance of this interaction (see Table 15 below). Finally, the highest dose of 244/PR8 completely prevented clinical disease caused by a ten-fold higher A/WSN challenge dose (100 $LD_{50}$), and converted 1000 $LD_{50}$ A/WSN into a transient disease with mild clinical signs (data not shown).

Duration of Prophylactic Protection Exerted by Protecting Virus

Figure 5:
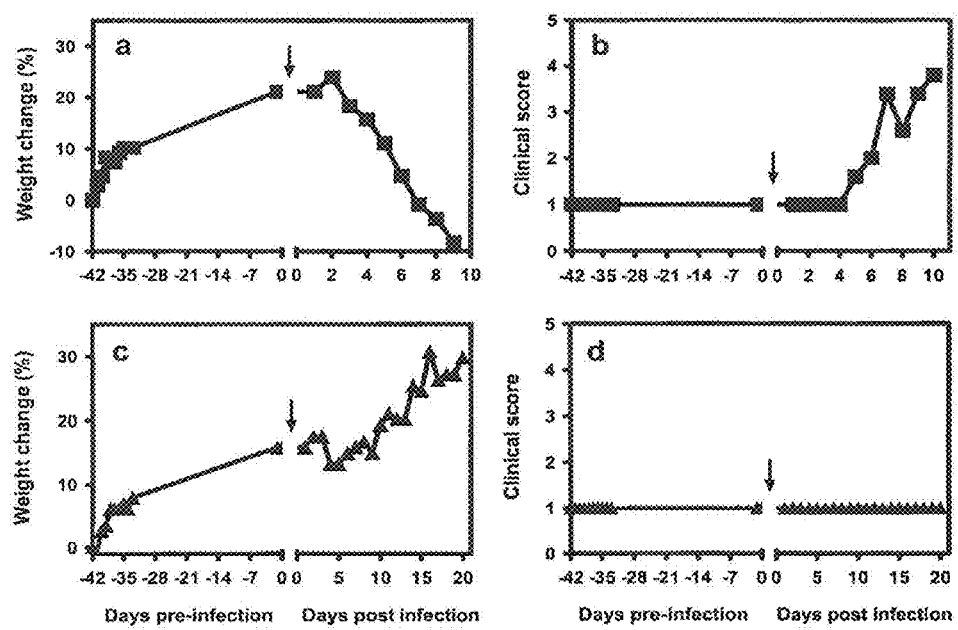
FIG. 5 shows the duration of prophylactic activity of 244/PR8 protecting virus

FIG. 5 shows the duration of prophylactic activity of 244/PR8 protecting virus. A single dose of protecting virus (a, b) or inactivated protecting virus (c, d) (4000 HAU/10 μg) was administered intranasally at 42 days (6 weeks) before infection: ■, inactivated protecting virus; ▲, protecting virus. Mice were challenged with 10 $LD_{50}$ A/WSN on day 0 (arrow). Mice were monitored by weight change (a, c) and summed clinical score (b, d).

A single dose of protecting virus or inactivated protecting virus (4000 HAU) has no deleterious effects and animals remain completely healthy and gain weight exactly like mock-inoculated controls (FIG. 5a, c). Mice were challenged intranasally with infectious virus 1 to 42 days (6 weeks) after receiving protecting virus. FIG. 5 shows data for the 6 week group. Mice that had received protecting virus were completely protected (FIG. 5c, d), while those given inactivated protecting virus succumbed to the infection (FIG. 5a, b).

Failure of the inactivated protecting virus to prevent disease showed that mice had not mounted an adaptive immune response to influenza virus antigens, and suggested that that protecting RNA persisted in the murine respiratory tract. This was tested by RT-PCR using RNA extracted from lungs of mice that had been inoculated only with protecting virus.

Figure 6:
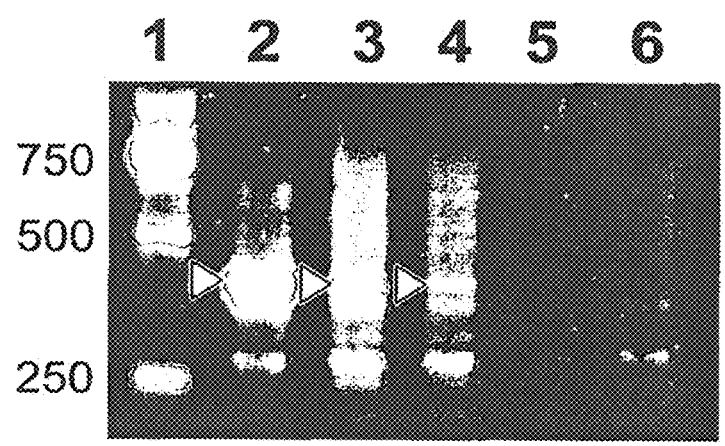
FIG. 6 shows the longevity of protecting RNA 244 (395 nt) in mouse lung in the absence of infectious virus, as demonstrated by RT-PCR with primers RNA1F and RNA1R.

FIG. 6 shows the longevity of protecting RNA 244 (395 nt) in mouse lung in the absence of infectious virus, as demonstrated by RT-PCR with primers RNA1F and RNA1R. Lane 1, DNA size markers (bp); lanes 2-6 amplicons from mouse lungs. RNA for lanes 2-5 was extracted 1 day, 9 days, 21 days and 42 days respectively after inoculation with 4000 HAU of protecting virus; lane 6, mock-inoculated.

RT-PCR shows that protecting RNA does persist, and appears to decline with time (FIG. 6). It was detected for up to 21 days post-inoculation, suggesting that protecting RNA was responsible for making mice refractory to clinical influenza. Mice given a 10-fold dilution of protecting virus (400 HAU) were completely protected from challenge 7 days later, but not 14 days later (data not shown).

Prophylaxis Extends to Different Subtypes of Influenza A Virus

One of the problems in combatting influenza is that there may be 144 distinct A virus subtypes, as well as the progressive drift variation that they all undergo in humans, and each subtype and significant drift variant requires its own vaccine. However, intranasally administered 244/PR8 protecting virus protected mice from clinical disease caused by human strains of H3N2 (A/England/939/69×A/PR/8/34), H2N2 (A/Jap/305/57), and the antigenically distinct H1N1 viruses (A/PR/8/34 and A/WS/33(N)) and the equine strain H3N8 (A/Newmarket/7339/79) (data not shown). Thus protecting virus affords broad protection that dose not appear to be limited by the H and N surface antigens.

Protecting Virus has Therapeutic Benefit

Previous work with non-cloned interfering virus showed no therapeutic effect, but because of the strong prophylactic action of defined protecting virus this experiment was revisited. Mice were infected with 10 $LD_{50}$ of A/WSN as before, and treated intranasally 24 and 48 h later with a single dose of protecting virus or control inactivated protecting virus (4000 HAU). While all control mice died, therapy with protecting virus at 24 h completely prevented clinical disease, weight loss and death; at 48 h all mice became ill although illness was delayed, and 33% recovered (Table 1b below). Increasing the infectious dose reduced therapeutic efficacy.

Table 1b shows the therapeutic benefit of protecting virus in mice[a]

TABLE 1b

| Therapy | Inactivated protecting virus | | Protecting virus | |
|---|---|---|---|---|
| | Sick | Recovered | Sick | Recovered |
| 24 h p.i. | 100% (by day 5) | 0% (died days 5-7) | 0% | 100% |
| 48 h p.i. | 100% (by day 5) | 0% (died days 5 + 7) | 100% | 33% (during days 6-16) |

[a] Infected with 10 $LD_{50}$ A/WSN and treated post infection (p.i.) at the times shown with inactivated protecting virus or protecting virus (4000 HAU/10 µg virus protein). All inoculations were intranasal with light anaesthesia. Groups of 5-7 mice were used; this experiment is representative of 3 independent experiments.

The following examples provide more specific detail of experiments involving cloned DI virus of the invention.

EXAMPLE 1

Production of Cloned DI Virus 220/PR8

Previous work known in the art teaches that the production of DI virus is optimal when embryonated hens' eggs are inoculated with large amounts of inoculum (e.g. up to 2 ml per egg). The explanation given is that cells in which non-infectious DI virus reside also need to receive infectious (helper) virus, so that the former can be replicated. Furthermore, the amount of DI virus present normally increases when the passage is repeated a second or third time. Eventually, the amount of DI virus generated exceeds the amount of infectious virus present, there is a lack of helper virus function, and total virus production declines.

Unexpectedly, it was found that by the inventor that inoculating embryonated chicken's eggs with routine, i.e. standard amounts of cloned DI influenza A virus fails to yield the expected quantities of DI virus material; so much so, that it is an impediment to further laboratory studies, including animal studies in vivo; let alone clinical trials or the production of DI virus preparations for manufacture of pharmaceutically acceptable compositions or vaccines.

Surprisingly, the inventor found that even a single passage of 100 µl of inoculum of a cloned DI virus in embryonated hens' eggs for 48 h at 33° C. gave a reasonably high yield of DI virus. In particular, DI virus 244/151PR8, gave a very high yield of virus (as shown by haemagglutination) when using just 100 µl of inoculum.

The inventor also found that by diluting the inoculum 1/10, just one passage of 100 µl of this in the allantoic cavity of 10-day-old embryonated hens' eggs gave an increase of total virus of approximately 10-fold (as shown by haemagglutination). An increase in protective virus yield achieved by a diluting the virus preparation prior to passage in embryonated hens' eggs was wholly unexpected.

Furthermore, when passaged virus obtained in high yield from diluted inoculum was purified and concentrated, this virus preparation was found to protect mice from a lethal intranasal challenge of A/WSN influenza virus. This demonstrated that the passaged virus preparation contained DI RNA.

A problem identified by the inventor was therefore how to amplify up potential cloned DI virus while maintaining a high (enough) virus yield.

The procedure employed was:

1. The plasmids needed for producing infectious helper influenza virus plus the plasmid encoding RNA 220 (62.5 ng) were transfected into HEK293T cells. Whilst HEK293T cells are useful for transfection they are not so useful for growing up quantities of cloned virus.

2. The transfected 293T cells were then cocultured with Madin-Derby canine kidney (MDCK) cells. Tissue culture fluids were removed after 2 days' incubation, tested for viral haemagglutinating activity, and frozen at −70° C. Whilst the MDCK cells are difficult to transfect, they are fairly good for growing influenza virus.

3. Tissue culture fluid from MDCK cells (500 µl/egg) was injected into the allantoic cavity of fertile hen's eggs to boost the virus titre (Passage (P) 0). Eggs were incubated at 33° C. for 24 h, and then chilled at 4° C. to kill the embryo. Allantoic fluid (that contains virus) was then removed from the egg, and tested for HA activity.

4. Virus was passaged serially in eggs (P1-3) using 200 µl inocula and 24 h incubation.

Table 1c below shows the yield of cloned DI virus 220/PR8 as a function of passage number TABLE 1c

| Experiment number | Host and passage (P) number | Inoculum (experiment number) | Volume of inoculum (µl) | Yield of virus (HAU/ml) |
|---|---|---|---|---|
| 774H(i) | 293T cells (transfection) | Plasmids | Not applicable | 32 |
| 774H(ii) | Egg-P0 | 774H(i) | 500 | 9600* |
| 778 | Egg-P1 | 774H(ii) | 200 | 8000 |
| 779 | Egg-P2 | 778 | 200 | 800 |
| 788 | Egg-P2 | 778 | 200 | 1600 |
| 780 | Egg-P3 | 779 | 200 | 400 |

HAU, haemagglutinating units.
*Yield of PR8 wt was ≥19 200 HAU/ml.

Note that HA titres were not done at the same time and that small variations in titre can arise depending on the age of the red blood cells.

A high virus titre/large volume inoculum was used in eggs for approximately 3 passages. (See P1 to P3 in table 1a) The titre obtained at P1 was comparable (actually approximately 2.4-fold lower) than that of a wild type virus. The titres obtained at P2 (two experiments) and P3 were 12- to 50-fold lower than wild type virus, i.e. not enough virus was present to be useable.

Table 2 below shows the yield of cloned DI virus 220/PR8 as a function of inoculum volume

TABLE 2

| Experiment number | Host and passage (P) number | Inoculum (experiment number) | Volume of inoculum (µl) | Yield of virus (HAU/ml) | DI activity* |
|---|---|---|---|---|---|
| 778 | Egg-P1 | 774H(ii) | 200 | 8000 | Not done |
| 794 | Egg-P1 | 774H(ii) | 10 | 4800 | ++++ |
| 802 | Egg-P1 | 774H(ii) | 1 | 4800 | Not done |
| 800 | Egg-P1 | 774H(ii) | 0.1 | 5000 | Not done |

*In mice from lethal challenge with A/WSN

Reducing the inoculum volume had little affect on the total virus yield, but the 10 µl inoculum appears both economical and practicable.

FIG. 3 shows the results of an experiment in which various amounts of 244 plasmid were transfected into 293T cells together with a constant amount of plasmids encoding infectious A/WSN. One day later these were cocultivated with MDCK cells for 7 days. Virus yield (HAU) in the culture fluid was measured. Virus yield proved sensitive to the amount of transfected defective RNA-expressing plasmid, and the amount of virus passaged in embryonated chickens eggs (data not shown). Better virus yields are obtained by inoculating less defective RNA plasmid, or passing smaller amounts of virus in embryonated eggs.

Successive egg passages gave a seed virus and the final virus stock respectively. After purification by differential centrifugation, defective viruses were normalised to $2 \times 10^5$ haemagglutination units (HAU)/ml.

EXAMPLE 2

Generation of Protecting Virus 244/PR8

The principal protecting RNA used (segment 1; RNA244) arose spontaneously during the transfection/cocultivation of plasmids encoding infectious A/PR/8/34 (Subbarao, K. et al 2003 Virology 305: 192-200). The DNA mix transfected into 293T cells contained 0.5 µg of each of the 8 A/PR8 gene segment (under PolI promoters), 0.5 µg each PB1 and PB2 expression plasmids, 0.1 µg PA expression plasmid, and 1 µg NP expression plasmid, and Fugene (Roche).

In order to optimize the transfection of the 244 iRNA plasmid, the 244 RNA was cloned into the PolI expression plasmid pPOLI-SapIT (Subbarao (2003) supra), so that a vRNA-sense transcript was expressed. Varying amounts of the 244 plasmid (0-0.5 µg) were transfected into 293T cells as described above. After 24 h, the 293T cells were trypsinized, mixed with MDCK cells and re-plated. After 7 days culture supernatants were harvested, and virus yield determined by HA assay.

In another experiment plasmids encoding A/WSN were used (Neumann, G. et al. 1999 Proc. Natl. Acad. Sci. 96: 9345-9350). After 24 h, the 293T cells were trypsinized, mixed with MDCK cells and re-plated, and culture supernatants harvested 7 days later. Growth of virus was determined by HA assay. This was passaged twice in embryonated chicken's eggs to make a seed stock, and then a working stock for mouse studies. Virus was purified by differential centrifugation through sucrose. Stocks were resuspended in PBS containing 0.1% w/v bovine serum albumen, standardized by HA titration, and stored in liquid nitrogen. RT-PCR and sequencing of RNA extracted from purified virus showed that the 244 RNA was derived by a single central deletion of approximately 80% from segment 1. The RNA is 395 nt, comprising nt 1-244 and 1891-2041 (of the minus-sense RNA). Thus it retains the exact termini and the terminal sequences that contain the replication and encapsidation signals. Analysis with primers specific for each genome segment showed that the 244 RNA was the only major defective RNA present. 244 RNA retained its sequence on passage and was not replaced or augmented by significant amounts of other defective RNAs.

Protecting viruses A/PR8 or A/Victoria/3/75 (A/Vic; H3N2) containing RNAs 220 or 317 (Duhaut, S. D. & Dimmock, N. J. 2003, Journal of Virological Methods 108: 75-82) were produced in the same way. Optimization of the amount of defective RNA plasmid during transfection (see below) and of the egg inoculum was required in order to avoid low yields of protecting virus. Infectious virus stocks of other influenza A viruses were produced by low multiplicity infection (approximately $10^4$ $EID_{50}$).

EXAMPLE 3

Production of Cloned DI Virus 244/151PR8

Allantoic fluid (10 µl/egg) was injected into the allantoic cavity of fertile hen's eggs to make a stock of DI virus. Eggs were incubated at 33° C. for 48 h, and then chilled at 4° C. to kill the embryo. Allantoic fluid was then removed, and tested for HA activity. Virus was purified by differential centrifugation at 4° C. Removal of large debris was by 'low-speed' centrifugation (3000 rpm for 10 min in the swing-out rotor of a Beckman GS-6R centrifuge). This was followed by pelleting virus 26000 rpm g for 2 h in a Beckman SW28 rotor) through a 5 ml cushion of sucrose (10% w/v in Tris-buffered saline pH 7.4) to separate virus from smaller contaminants. Low density lipid-containing material (e.g. egg yolk) is retained on the sucrose. The HA of the virus was then titrated and adjusted to $2 \times 10^5$ HAU/ml. This was stored in aliquots in liquid nitrogen or at –70° C.

Table 3 below shows results for the production of cloned DI virus 244/151PR8

TABLE 3

| Experiment number | Host | Inoculum | Volume of inoculum (µl) | Yield of virus (HAU/ml) | DI activity* |
|---|---|---|---|---|---|
| 781 | 293T cells (transfection) | Plasmids | Not applicable | 512 | Not done |
| 783 | P0-egg | 781 | 200 | ? | Not done |
| 793 | P1-egg | 783 | 10 | 3200 | ++++ |
| 797 | P1-egg | 783 | 10 | 3800 | ++++ |

P0, passage zero.
*In mice from lethal challenge with A/WSN; both were +++ protective at $1/100$. Thus DI activity was produced reproducibly on egg passage.

EXAMPLE 4

Titration of 244/151PR8 DI Activity in Mice

Infectivity titres were determined as required by titration in cell culture, eggs, and mice. Virus was plaque assayed in MDCK cells under agar by standard procedures. Eggs were inoculated with limit-diluted virus and incubated for 3 days. Virus-positive eggs were identified by HA in allantoic fluid. Mice were inoculated as described below, then 3 days later mice were killed, and ground lungs from individual mice were inoculated into eggs, and the presence of virus was determined by HA. Alternatively mice were challenged intranasally after 3 weeks with homologous virus to determine if subclinical infection had stimulated protective immunity. Egg and mouse end-point infectivity titres were calculated according to Spearman-Kärber (Karber, G. in *Textbook of Virology* (eds. Rhodes, A. J. & van Rooyen, C. E.) 118 (Williams and Wilkins Co., Baltimore, 1968)).

Adult C3H/He-mg (H-$2^k$) mice (4-week-old; 16-20 g) were inoculated intranasally under light ether anaesthesia as previously described (Noble et al, 2004 Vaccine 22: 3018-3025) with a 40 µl inoculum divided between the two nares. Helper virus infectivity can be eliminated without reducing protection by a short (20 s) burst of UV irradiation at 253.7 nm because of the difference in UV-target sizes—13,600 nt for infectivity and 395 nt for the protecting RNA. The lamp was calibrated by inactivating A/PR8 infectivity. Longer UV irradiation (8 minutes) inactivates protection and provides a preparation that controlled for any immune system-stimulating or receptor-blocking effects. Irradiation did not affect H or N activities. Mice were given various combinations of non-infectious protecting virus, inactivated protecting virus, infectious challenge virus, or diluent. Infectious challenge viruses were titrated in mice to determine a dose for each that caused comparable respiratory disease. Mice were infected with 10 $LD_{50}$ (100 $ID_{50}$) of A/WSN as determined by immunization by the intranasal route. The health of mice was assessed by loss of weight, and by previously described clinical criteria (Noble, S. & Dimmock, N. J., 1994 Journal of General Virology 75: 3485-3491). Mice were weighed as a group. Clinical criteria were scored as follows: 1 point for each healthy mouse; 2 points for a mouse showing signs of malaise, including some piloerection, slightly changed gait, and increased ambulation: 3 points for a mouse showing signs of strong piloerection, constricted abdomen, changed gait, periods of inactivity, increased breathing rate, and sometime râles; 4 points for a mouse with enhanced characteristics of the previous group, but showing little activity, and becoming moribund; such mice were killed when it was clear that they would not survive; and 5 points for a dead mouse. To allow comparison, the total clinical score was divided by the number of mice in the experimental group. All viruses caused similar clinical disease, including lung consolidation. Experiments followed the guidelines of the UK Coordinating Committee for Cancer Research.

EXPERIMENT 1

Protection of Mice from Lethal A/WSN by 400 HAU of DI Virus

Table 4 below shows the results for mice inoculated intranasally with 400 HAU (approximately 1 μg virus protein) of UV-inactivated DI virus mixed with challenge A/WSN virus or with DI virus mixed with challenge A/WSN virus. Mice were also inoculated with DI virus alone. Mice were inoculated after light ether anaesthesia.

TABLE 4

| | iDIV + virus[a] | | | DIV + virus[a] | | | DIV alone[b] | | |
|---|---|---|---|---|---|---|---|---|---|
| Day | Weight | Sick | Dead | Weight | Sick | Dead | Weight | Sick | Dead |
| 0 | 107 | 0 | 0 | 115 | 0 | 0 | 49 | 0 | 0 |
| 1 | 108 | 0 | 0 | 116 | 0 | 0 | 52 | 0 | 0 |
| 2 | 109 | 0 | 0 | 117 | 0 | 0 | 48 | 0 | 0 |
| 3 | 110 | 0 | 0 | 119 | 0 | 0 | 50 | 0 | 0 |
| 4 | 106 | 3 | 0 | 119 | 0 | 0 | 50 | 0 | 0 |
| 5 | 102 | 5 | 0 | 121 | 0 | 0 | 51 | 0 | 0 |
| 6 | 94 | 5 | 0 | 124 | 0 | 0 | 53 | 0 | 0 |
| 7 | 86 | 1 | 4 | 122 | 0 | 0 | 52 | 0 | 0 |
| 8 | 17 | 1 | | 125 | 0 | 0 | 53 | 0 | 0 |
| 9 | 17 | 1 | | 127 | 0 | 0 | 54 | 0 | 0 |
| 10 | 17 | 1 | | 129 | 0 | 0 | 55 | 0 | 0 | iDIV = UV-inactivated DI virus;
DIV = DI virus.
[a]5 mice/group;
[b]2 mice/group All mice given inactivated DI virus plus challenge virus lost weight and became sick; 80% died. All mice given DI virus plus challenge virus remained clinical normal. They gained weight every day, apart from day 7.

EXPERIMENT 2

Challenge of all Mice Surviving at 3 Weeks after Inoculation with High Dose A/WSN (Approximately 1000 $LD_{50}$)

Table 5 below shows the result of taking the 3 week survivors of Experiment 1 above and challenging them with a high dose of A/WSN.

TABLE 5

| | iDIV + virus | | | DIV + virus[a] | | | DIV alone[b] | | |
|---|---|---|---|---|---|---|---|---|---|
| Day | Weight | Sick | Dead | Weight | Sick | Dead | Weight | Sick | Dead |
| 0 | n/a | | | 163 | 0 | 0 | 65 | 0 | 0 |
| 1 | | | | 165 | 0 | 0 | 66 | 0 | 0 |
| 2 | | | | 166 | 0 | 0 | 63 | 0 | 0 |
| 3 | | | | 166 | 0 | 0 | 58 | 2 | 0 |
| 4 | | | | 169 | 0 | 0 | 55 | 2 | 0 |
| 5 | | | | 170 | 0 | 0 | 53 | 2 | 2 |
| 6 | | | | 169 | 0 | 0 | 50 | | 2 |
| 7 | | | | 171 | 0 | 0 | | | |
| 8 | | | | 172 | 0 | 0 | | | |
| 9 | | | | 173 | 0 | 0 | | | |
| 10 | | | | 173 | 0 | 0 | | | | iDIV = UV-inactivated DI virus
DIV = DI virus
[a]5 mice/group;
[b]2 mice/group

Mice that had previously received DI virus alone lost weight and died on day 6. This suggests that DI virus was no longer present or not able to withstand the high dose of challenge virus.

Mice that had previously received DI virus plus challenge virus gained weight and remained well, suggesting that they had acquired immunity to A/WSN.

EXPERIMENT 3

Protection of Mice from Lethal A/WSN by 40 HAU DI Virus

Table 6 shows the result of mice inoculated intranasally with 40 HAU (approximately 100 ng virus protein) of UV-inactivated DI virus mixed with challenge A/WSN virus or with DI virus mixed with challenge A/WSN virus. Mice were also given DI virus alone (2/group). Mice were inoculated after light ether anaesthesia.

TABLE 6

| | iDIV + virus[a] | | | DIV + virus[b] | | | DIV alone[c] | | |
|---|---|---|---|---|---|---|---|---|---|
| Day | Weight | Sick | Dead | Weight | Sick | Dead | Weight | Sick | Dead |
| 0 | 64 | 0 | 0 | 78 | 0 | 0 | 42 | 0 | 0 |
| 1 | 66 | 0 | 0 | 80 | 0 | 0 | 43 | 0 | 0 |
| 2 | 67 | 0 | 0 | 83 | 0 | 0 | 44 | 0 | 0 |
| 3 | 67 | 0 | 0 | 86 | 0 | 0 | 47 | 0 | 0 |
| 4 | 66 | 0 | 0 | 87 | 0 | 0 | 46 | 0 | 0 |
| 5 | 63 | 1 | 0 | 88 | 0 | 0 | 47 | 0 | 0 |
| 6 | 57 | 4 | 0 | 85 | 0 | 0 | 47 | 0 | 0 |
| 7 | 54 | 4 | 0 | 82 | 4 | 0 | 49 | 0 | 0 |
| 8 | 51 | 3 | 0 | 85 | 2 | 0 | 50 | 0 | 0 |
| 9 | 39 | 3 | 1 | 85 | 2 | 0 | 50 | 0 | 0 |
| 10 | 15 | 1 | 2 | 88 | 0 | 0 | 51 | 0 | 0 |
| 11 | 14 | | 1 | 89 | 0 | 0 | 52 | 0 | 0 | iDIV = UV-inactivated DI virus

DIV = DI virus.

[a]4 mice/group;

[b]5 mice/group;

[c]2 mice/group

All mice given inactivated DI virus plus challenge virus lost weight, became sick, and died. Mice given DI virus plus challenge virus developed a delayed and mild clinical disease (days 7-9) that rapidly resolved. They had slight temporary weight loss (days 6 and 7).

EXPERIMENT 4

Protection of Mice from Lethal A/WSN by 4 HAU DI Virus

Table 7 below shows the results of mice inoculated intranasally with 4 HAU (approximately 10 ng virus protein) of UV-inactivated DI virus mixed with challenge A/WSN virus or with DI virus mixed with challenge A/WSN virus. Mice were also DI virus alone (2/group). Mice were inoculated after light ether anaesthesia.

TABLE 7

| | iDIV + virus[a] | | | DIV + virus[b] | | |
|---|---|---|---|---|---|---|
| Day | Weight | Sick | Dead | Weight | Sick | Dead |
| 0 | 64 | 0 | 0 | 83 | 0 | 0 |
| 1 | 66 | 0 | 0 | 85 | 0 | 0 |
| 2 | 67 | 0 | 0 | 88 | 0 | 0 |
| 3 | 67 | 0 | 0 | 90 | 0 | 0 |
| 4 | 66 | 0 | 0 | 88 | 0 | 0 |
| 5 | 63 | 1 | 0 | 88 | 0 | 0 |
| 6 | 57 | 4 | 0 | 80 | 3 | 0 |
| 7 | 54 | 4 | 0 | 75 | 5 | 0 |
| 8 | 51 | 3 | 0 | 71 | 5 | 0 |

TABLE 7-continued

| | iDIV + virus[a] | | | DIV + virus[b] | | |
|---|---|---|---|---|---|---|
| Day | Weight | Sick | Dead | Weight | Sick | Dead |
| 9 | 39 | 3 | 1 | 68 | 5 | 0 |
| 10 | 15 | 1 | 2 | 54 | 3 | 2 |
| 11 | 14 | | 1 | 44 | 2 | 0 | iDIV = UV-inactivated DI virus
DIV = DI virus
[a]40 HAU/mouse; 5 mice/group
[b]4 HAU/mouse; 5 mice/group All mice given inactivated DI virus plus challenge virus lost weight, became sick, and died. All mice given 4 HAU of DI virus plus challenge virus developed clinical disease with weight loss. 3/5 mice (60%) survived after 11 days indicating weak protection at this low dose of DI virus. However 1 mouse sickened and died on day 16.

EXPERIMENT 5

Challenge of all Mice Surviving at 3 Weeks after Inoculation with High Dose A/WSN Table 8 below shows the results of an experiment using the survivors of Experiments 3 and 4 above. These survivors were challenged with approximately 1000 $LD_{50}$ of A/WSN

TABLE 8

| | iDIV + virus[a] | | | DIV + virus[b] | | | DIV alone[c] | | |
|---|---|---|---|---|---|---|---|---|---|
| Day | Weight | Sick | Dead | Weight | Sick | Dead | Weight | Sick | Dead |
| 0 | 105 | 0 | 0 | 40 | 0 | 0 | 59 | 0 | 0 |
| 1 | 108 | 0 | 0 | 41 | 0 | 0 | 61 | 0 | 0 |
| 2 | 109 | 0 | 0 | 42 | 0 | 0 | 59 | 2 | 0 |
| 3 | 110 | 0 | 0 | 44 | 0 | 0 | 51 | 2 | 0 |
| 4 | 109 | 0 | 0 | 44 | 0 | 0 | 48 | 1 | 1 |
| 5 | 109 | 0 | 0 | 44 | 0 | 0 | 22 | | 1 |
| 6 | 111 | 0 | 0 | 45 | 0 | 0 | | | |
| 7 | 113 | 0 | 0 | 45 | 0 | 0 | | | |
| 8 | 115 | 0 | 0 | 47 | 0 | 0 | | | |
| 9 | 118 | 0 | 0 | 46 | 0 | 0 | | | |
| 10 | 119 | 0 | 0 | 45 | 0 | 0 | | | | iDIV = UV-inactivated DI virus

DIV = DI virus.

[a]40 HAU/mouse; 5 mice/group.

[b]4 HAU/mouse; 2 mice/group.

[c]40 HAU/mouse; 2 mice/group.

Mice that received DI virus alone lost weight and died by day 6. This suggested that DI virus was no longer present or not able to withstand the high dose of challenge virus.

All mice that received 40 HAU of DI virus plus challenge virus gained weight and remained well, suggesting that they had acquired immunity to A/WSN.

The 2 mice that received 4 HAU of DI virus plus challenge virus and survived gained weight and remained well, suggesting that they had acquired immunity to A/WSN.

EXAMPLE 5

Duration of 244/151PR8-Mediated Protection in Mice

Table 9 below shows how 4000 HAU of 244/151PR8 alone protects mice for at least 6 weeks.

The timeline of inoculation of mice was as follows:
Day 0: DI virus
Week 6: infectious challenge A/WSN to determine protection
Week 9: high dose infectious challenge A/WSN to determine immune status
Weights of mice were monitored for 8 days after Day 0.

TABLE 9

|     | iDIV[a] | | | DIV[a] | | | DIV[b] | | |
| --- | --- | --- | --- | --- | --- | --- | --- | --- | --- |
| Day | Weight | Sick | Dead | Weight | Sick | Dead | Weight | Sick | Dead |
| 0 | 109 | 0 | 0 | 114 | 0 | 0 | 71 | 0 | 0 |
| 1 | 112 | 0 | 0 | 113 | 0 | 0 | 72 | 0 | 0 |
| 2 | 114 | 0 | 0 | 117 | 0 | 0 | 73 | 0 | 0 |
| 3 | 118 | 0 | 0 | 118 | 0 | 0 | 73 | 0 | 0 |
| 4 | 117 | 0 | 0 | 121 | 0 | 0 | 75 | 0 | 0 |
| 5 | 119 | 0 | 0 | 121 | 0 | 0 | 75 | 0 | 0 |
| 6 | 120 | 0 | 0 | 121 | 0 | 0 | 77 | 0 | 0 |
| 7 | 121 | 0 | 0 | 122 | 0 | 0 | 79 | 0 | 0 |
| 8 | 120 | 0 | 0 | 121 | 0 | 0 | 78 | 0 | 0 |
| 9 | 120 | 0 | 0 | 123 | 0 | 0 | 80 | 0 | 0 | iDIV = UV-inactivated DI virus
DIV = DI virus
[a]6 mice/group
[b]3 mice/group

DI virus alone had no deleterious affect on weight gain or clinical status.

Table 10 below shows the effect of a primary challenge with infectious A/WSN alone or diluent 6 weeks after administration of the DI virus (above). Mice were monitored for 10 days after the start of week 6.

TABLE 10

|     | Virus after iDIV[a] | | | Virus after DIV[b] | | | Diluent after DIV[c] | | |
| --- | --- | --- | --- | --- | --- | --- | --- | --- | --- |
| Day | Weight | Sick | Dead | Weight | Sick | Dead | Weight | Sick | Dead |
| 0 | 132 | 0 | 0 | 136 | 0 | 0 | 71 | 0 | 0 |
| 1 | 132 | 0 | 0 | 132 | 0 | 0 | 71 | 0 | 0 |
| 2 | 135 | 0 | 0 | 134 | 0 | 0 | 71 | 0 | 0 |
| 3 | 129 | 0 | 0 | 134 | 0 | 0 | 71 | 0 | 0 |
| 4 | 121 | 0 | 0 | 129 | 0 | 0 | 72 | 0 | 0 |
| 5 | 114 | 3 | 0 | 129 | 0 | 0 | 71 | 0 | 0 |
| 6 | 108 | 5 | 0 | 131 | 0 | 0 | 70 | 0 | 0 |
| 7 | 105 | 5 | 0 | 132 | 0 | 0 | 70 | 0 | 0 |
| 8 | 82 | 5 | 0 | 133 | 0 | 0 | 73 | 0 | 0 |
| 9 | 80 | 4 | 1 | 131 | 0 | 0 | 73 | 0 | 0 |
| 10 | 62 | 3 | 1 | 136 | 0 | 0 | 74 | 0 | 0 | iDIV = UV-inactivated DI virus
DIV = DI virus.
[a]5 mice/group
[b]2 mice/group

Mice challenged 6 weeks after being given inactivated DI virus lost weight, became ill, and died. Mice challenged 6 weeks after being given DI virus continued to gain weight (apart from a slight loss on days 4 and 5) and showed no clinical disease.

Table 11 below shows the results of challenging the mice (above) free of clinical disease (and which gained weight overall) with a high dose (approximately 1000 $LD_{50}$) of A/WSN alone. The mice were monitored for immune status for 10 days subsequent to the start of week 9.

TABLE 11

| Day | Virus after iDIV[a] | | | Virus after DIV[a] | | | Virus alone[b] | | |
|---|---|---|---|---|---|---|---|---|---|
| | Weight | Sick | Dead | Weight | Sick | Dead | Weight | Sick | Dead |
| 0 | Not done as still ill | | | 147 | 0 | 0 | 55 | 0 | 0 |
| 1 | | | | 149 | 0 | 0 | 54 | 0 | 0 |
| 2 | | | | 149 | 0 | 0 | 53 | 2 | 0 |
| 3 | | | | 148 | 0 | 0 | 47 | 2 | 0 |
| 4 | | | | 150 | 0 | 0 | 45 | 2 | 0 |
| 5 | | | | 151 | 0 | 0 | 42 | 1 | 1 |
| 6 | | | | 153 | 0 | 0 | 18 | | 1 |
| 7 | | | | 153 | 0 | 0 | | | |
| 8 | | | | 156 | 0 | 0 | | | |
| 9 | | | | 155 | 0 | 0 | | | |
| 10 | | | | 157 | 0 | 0 | | | | iDIV = UV-inactivated DI virus;
DIV = DI virus.
[a]5 mice/group.
[b]2 mice/group; control for challenge virus; not inoculated before Compared to a control (no DIV treatment), the previously DIV treated mice resisted high dose lethal challenge showing that they had acquired immunity to A/WSN.

EXAMPLE 6

244/151PR8 is Weakly Therapeutic when Given 21 h after Infection

Table 12 below shows the results of infecting mice with A/WSN followed by administration of 244/151PR8 after a further 21 hours or 48 hours (not shown).

TABLE 12

| Day | Virus followed by iDIV at 21 h[a] | | | Virus followed by DIV at 21 h[a] | | | Diluent followed by DIV at 21 h[b] | | |
|---|---|---|---|---|---|---|---|---|---|
| | Weight | Sick | Dead | Weight | Sick | Dead | Weight | Sick | Dead |
| 0 | 132 | 0 | 0 | 129 | 0 | 0 | 31 | 0 | 0 |
| 1 | 135 | 0 | 0 | 132 | 0 | 0 | 31 | 0 | 0 |
| 2 | 131 | 3 | 0 | 135 | 0 | 0 | 34 | 0 | 0 |
| 3 | 116 | 7 | 0 | 137 | 0 | 0 | 36 | 0 | 0 |
| 4 | 108 | 7 | 0 | 138 | 0 | 0 | 39 | 0 | 0 |
| 5 | 101 | 4 | 3 | 131 | 1 | 0 | 40 | 0 | 0 |
| 6 | 29 | | 4 | 118 | 7 | 0 | 41 | 0 | 0 |
| 7 | | | | 110 | 2 | 5 | 43 | 0 | 0 |
| 8 | | | | 35 | 2 | | 43 | 0 | 0 |
| 9 | | | | 36 | 2 | | 44 | 0 | 0 |
| 10 | | | | 35 | 2 | | 44 | 0 | 0 | iDIV = UV-inactivated DI virus
DIV = DI virus.
[a]7 mice/group.
[b]2 mice/group.

Treatment with DI virus 21 h after A/WSN infection delayed weight loss and clinical disease in the mice by 2 days. 2/7 mice (29%) recovered compared with 0/7 of mice given an inactivated DI virus. However, this was an unusually strong challenge, with 100% mice becoming ill by day 3. DI virus gave no protection when given 48 hours after infection.

EXAMPLE 7

A High Dose of 244/151PR8 Prevents Primary Infection, Disease and Death Caused by A/WSN Table 13 below shows results in which a high dose of 244/151PR8 prevents primary infection, disease and death caused by A/WSN, but results in poor conventional immunity to high dose A/WSN challenge, compared to the immunity resulting from administration of more dilute DI virus.

Time Line of Inoculations:

Day 0: mice inoculated with a mix of DI virus+A/WSN (primary infection). All mice were protected apart from some mice (3/5) given 4 HAU (column 3).

Day 21: mice were challenged with a high dose (approximately 1000 $LD_{50}$) of A/WSN challenge virus. Data is shown in Table 13 (columns 5-7) below.

TABLE 13

| Dose of DI virus (HAU) | Batch # | Experiment # | Primary infection No. dead/no. infected | Weight loss | High dose challenge | |
|---|---|---|---|---|---|---|
| | | | | | No. ill/no. challenged | No. dead/no. challenged |
| 4000 | 793 | 3477 | 0/7 | Yes | 5/7 (71%)* | 4/7 (57%)* |
| | 793 | 3528 | 0/4 | Yes | 4/4 (100%) | 2/4 (50%) |
| | 797 | 3563 | 0/4 | Yes | 4/4 (100%) | 3/4 (75%) |
| 400 | 793 | 3487 | 0/4 | No | 0/4 | |
| | 797 | 3563 | 0/4 | No | 0/4 | |
| 40 | 793 | 3498 | 0/5 | No | 0/5 | |
| | 793 | 3563 | 0/4 | No | 0/4 | |
| | 797 | 3512 | 0/4 | No | 0/4 | |
| 4 | 793 | 3512 | 2/5 | No | 0/2 | |

*mean = 87% ill and 60% dead.

The highest concentration of DI virus (4000 HAU/mouse or 1/1 dilution) protects animals from A/WSN but does not render them immune to a subsequent challenge; however lesser amounts of DI virus (1/10 and 1/100) both protect and permit immunity to A/WSN to develop. 1/1000 DI virus gives about 50% protection from the primary infection, and surviving mice are immune to challenge.

Without wishing to be bound by any particular theory, it may be that the highest concentration of DI virus reduced the multiplication of A/WSN from the primary injection to such a degree that it was not immunizing.

The experiment demonstrates the efficacy of DI virus and shows that the dose of DI virus will need to be adjusted so that it permits immunity to develop. Too much DI virus could be counterproductive in terms of developing immunity in an individual.

EXAMPLE 8

Relative Activity of DI Viruses in Mice Against A/WSN Challenge Virus

DI viruses were purified and standardized according to their haemagglutinating activity (which is directly proportional to the number of virus particles present). A titration of DI virus activity was carried out in mice over a 1000-fold dose range with A/WSN challenge virus. Mice were inoculated simultaneously with graded doses of DI virus+A/WSN or UV-inactivated DI virus+A/WSN (data not shown) and their weight and clinical status monitored. Most mice receiving inactivated DI virus+A/WSN suffered weight loss of >20% of body weight, severe clinical disease, and died. Table 14 below shows that protected mice (++++) were virtually indistinguishable from mock-inoculated controls.

TABLE 14

| HAU/mouse | 244/151PR8[a,b] | | 220/Vic | | 220/PR8 | 317/Vic |
|---|---|---|---|---|---|---|
| | 793 | 797 | 792 | 798 | 794 | 796 |
| 4000 | ++++/3477 | ++++/3563 | ++++/3415 | ++++/3588 | ++++/3511 | ++++/3517 |
| | ++++/3528 | | ++++/3527 | | | +++/3554 |
| 400 | ++++/3487 | ++++/3563 | ++++/3498 | +++/3588 | +/3511 | +++/3517 |
| 40 | ++++/3498 | +++/3563 | | −/3588 | +/3511 | −/3517 |
| | +++/3512 | | | | | |
| 4 | +/3512 | | | | | |

[a]DI virus with its batch number below; note that 793 and 797 are independent preparations made from the same source.
[b]Protection ranges from no weight loss or clinical disease (++++), through degrees of weight loss and clinical disease (+++ to +), to weight loss and clinical disease that did not differ from control mice given inactivated DI virus + A/WSN (−). '3477' etc are experiment numbers.
PR8 (A/Puerto Rico/8/34 (H1N1)) and Vic (A/Victoria/3/75 (H3N2)) are the helper viruses.

The most active DI virus is 244/151PR8, which protects mice almost completely down to 40 HAU (100 ng virus protein) per mouse. This result was repeated with 2 independent preparations of 244/151PR8.

The activity of the DI viruses ranged from 10-fold less with 220/Vic to 100-fold less with 220/PR8. Protection followed the order:

244/151PR8>220/Vic>317/Vic>220/PR8.

Whilst this does not affect the results and conclusions drawn, HAU gives only an approximate measure of the amount of DI virus e.g. it measures both DI and helper viruses.

Table 15 below shows a summary of 2-4 independent experiments comparing the prophylactic activity in mice mediated by various defined protecting viruses against infectious influenza virus.

TABLE 15

| Total protecting virus per mouse (HAU)[a] | 244/PR8 | 244/WSN | 220/PR8 | 220/Vic | 317/Vic |
|---|---|---|---|---|---|
| 4000 | ++++[b] | ++++ | ++++ | ++++ | ++++ |
| 400 | ++++ | ++++ | + | +++ | +++ |
| 40 | ++++ | ++++ | + | − | − |
| 4 | ++ | ++ | nd | nd | nd |
| 0[c] | − | − | − | − | − |

TABLE 15-continued

| Total protecting virus per mouse (HAU)[a] | 244/PR8 | 244/WSN | 220/PR8 | 220/Vic | 317/Vic |
|---|---|---|---|---|---|
| Minimum dose required for solid protection[d] | 0.1 μg[e] | 0.1 μg[e] | 10 μg | 1 μg | 1 μg |

[a]Given as a single intranasal dose under light anaesthesia simultaneously with 10 $LD_{50}$ of A/WSN challenge virus.
[b]The scale ranges from complete protection from weight loss and clinical disease (++++) to no difference to the controls given inactivated protecting virus plus challenge virus (−).
[c]Mice were given 4000 HAU of inactivated protecting virus.
[d]Defined as the smallest dose of protecting virus effecting +++ protection or better.
[e]Total virus protein inoculated per mouse
Nd, not done; groups of 5-7 mice were used; this experiment is representative of 2-4 independent experiments.

EXAMPLE 9

Treatment of Mice with 244/PR8 Protecting Virus at 24 h after Infection

Treatment of infected mice, carried out earlier, with non-defined protecting virus had no therapeutic benefit. Mice were inoculated by intranasal instillation (as described in previous examples) with infectious A/WSN virus (approximately 2.5 $MLD_{50}$ (50% mouse lethal dose) Approximately 24 h later the inoculated mice were treated with a single dose of control UV-inactivated DI virus or with active DI virus (both at 4000 HAU which is approximately 10 μg virus protein). Non-infected mice were also inoculated with DI virus. All inoculations were made (as described in previous examples) under light ether anaesthesia.

Table 16 below shows the fate of mice given a low dose of infecting virus, followed by administration of DI virus 24 h later against a control of administration of inactivated DI virus. A further control of non-infected mice was run whereby DI virus alone was administered.

TABLE 16

| Day of infection | Virus + iDI virus 24 h after infection[a] | | | Virus + DI virus 24 h after infection[a] | | | DI virus 24 h after infection[b] | | |
|---|---|---|---|---|---|---|---|---|---|
| | Weight | Sick | Dead | Weight | Sick | Dead | Weight | Sick | Dead |
| 0 | 114 | 0 | 0 | 114 | 0 | 0 | 35 | 0 | 0 |
| 1 | 114 | 0 | 0 | 116 | 0 | 0 | 36 | 0 | 0 |
| 2 | 112 | 0 | 0 | 112 | 0 | 0 | 35 | 0 | 0 |
| 3 | 106 | 6 | 0 | 112 | 0 | 0 | 35 | 0 | 0 |
| 4 | 102 | 6 | 0 | 116 | 0 | 0 | 38 | 0 | 0 |
| 5 | 95 | 5 | 1 | 116 | 0 | 0 | 37 | 0 | 0 |
| 6 | 74 | 3 | 3 | 117 | 0 | 0 | 36 | 0 | 0 |

TABLE 16-continued

| Day of infection | Virus + iDI virus 24 h after infection[a] | | | Virus + DI virus 24 h after infection[a] | | | DI virus 24 h after infection[b] | | |
|---|---|---|---|---|---|---|---|---|---|
| | Weight | Sick | Dead | Weight | Sick | Dead | Weight | Sick | Dead |
| 7 | 31 | | 2 | 119 | 0 | 0 | 37 | 0 | 0 |
| 8 | | | | 115 | ?1 | 0 | 37 | 0 | 0 |
| 9 | | | | 116 | ?1 | 0 | 38 | 0 | 0 |
| 10 | | | | 117 | 0 | 0 | 38 | 0 | 0 |
| 11 | | | | 117 | ?2 | 0 | 37 | 0 | 0 |
| 12 | | | | 118 | ?1 | 0 | 37 | 0 | 0 |
| 13 | | | | 118 | 0 | 0 | 37 | 0 | 0 |
| 14 | | | | 121 | 0 | 0 | 39 | 0 | 0 | iPV, UV-inactivated protecting virus; DI, defective interfering virus; weight is in grams; numbers of sick/dead mice in each group occurring each day are shown. The (?) refers to mice that may have been ill, but were not definitely ill.
[a]6 mice/group;
[b]2 mice/group).

All infected mice treated with control inactivated DI virus lost weight, and became ill on day 3 after infection. All mice were dead by day 7.

Infected mice treated with DI virus lost a little weight and/or stopped gaining weight, but remained clinically normal over the period that the control group were dying. There was possible mild illness on days 8, 9, 11 and 12, but this was transient. All mice (100%) were healthy at the end of the experiment.

At 3 weeks after infection, the mice that had been protected with DI virus (column 2 in Table 16 above) were challenged intranasally with a strong lethal dose of A/WSN. Mice were completely unaffected as judged by weight and clinical signs, whereas control mice that had not before experienced any influenza virus all died. The dose of virus used is too large for DI virus to protect against, thus these data suggest that the mice had developed an adaptive immunity to A/WSN although they had not become definitely ill during the first infection.

Table 17 below shows the fate of mice given an intermediate dose (approximately 5 $MLD_{50}$ of infecting A/WSN virus, followed by administration of DI virus 24 h later against a control of administration of inactivated DI virus (both at 4000 HAU which is approximately 10 µg virus protein). A further control of non-infected mice was run whereby DI virus alone was administered.

TABLE 17

| Day of infection | Virus + iDI virus 24 h after infection[a] | | | Virus + DI virus 24 h after infection[a] | | | DI virus 24 h after infection[b] | | |
|---|---|---|---|---|---|---|---|---|---|
| | Weight | Sick | Dead | Weight | Sick | Dead | Weight | Sick | Dead |
| 0 | 114 | 0 | 0 | 115 | 0 | 0 | 45 | 0 | 0 |
| 1 | 114 | 0 | 0 | 114 | 0 | 0 | 45 | 0 | 0 |
| 2 | 113 | 0 | 0 | 109 | 0 | 0 | 43 | 0 | 0 |
| 3 | 108 | 0 | 0 | 106 | 0 | 0 | 40 | 0 | 0 |
| 4 | 101 | 4 | 0 | 103 | 4 | 0 | 38 | 1 | 0 |
| 5 | 93 | 6 | 0 | 104 | 3 | 0 | 38 | 1 | 0 |
| 6 | 88 | 1 | 5 | 104 | 1 | 0 | 38 | 1 | 0 |
| 7 | 14 | 1 | 0 | 101 | 5 | 0 | 37 | 0 | 1 |
| 8 | 13 | | 1 | 98 | 6 | 0 | 21 | 0 | 0 |
| 9 | | | 0 | 94 | 4 | 1 | 22 | 0 | 0 |
| 10 | | | 0 | 81 | 3 | 1 | 22 | 0 | 0 |
| 11 | | | 0 | 70 | 2 | 0 | 22 | 0 | 0 |
| 12 | | | 0 | 72 | 2 | 0 | 22 | 0 | 0 |
| 13 | | | 0 | 72 | 1 | 0 | 22 | 0 | 0 |
| 14 | | | 0 | 76 | 1 | 0 | 22 | 0 | 0 |
| 15 | | | 0 | 78 | 1 | 0 | 23 | 0 | 0 |
| 16 | | | 0 | 79 | 1 | 0 | 23 | 0 | 0 |
| 17 | | | 0 | 79 | 0 | 0 | 24 | 0 | 0 | iDI, UV-inactivated defective interfering virus; DI, defective interfering.
[a]6 mice/group;
[b]2 mice/group).

All infected mice treated with control inactivated DI virus lost weight, and became sick by day 5. Most (83%) of the mice were dead (or culled) by day 6. All were dead by day 8.

Infected mice treated with DI virus lost weight and suffered some clinical disease at the same time as the control infected group. However clinical disease was milder, occurred over a more extended period, and took place in 2 episodes that peaked on days 4 and 8. Two mice died (on days 9 and 10), and the rest (4/6 or 67%) recovered.

One of the mice inoculated with PV alone became ill and died. This is a very unusual occurrence—the only time over several years' work that this has happened.

Table 18 below shows the fate of mice given a higher dose (approximately 10 $MLD_{50}$ of infecting A/WSN virus, followed by administration of DI virus 24 h later against a control of administration of inactivated DI virus (both at 4000 HAU which is approximately 10 µg virus protein). A further control of non-infected mice was run whereby DI virus alone was administered.

TABLE 18

| Day of infection | Virus + iDI virus 24 h after infection[a] | | | Virus + DI virus 24 h after infection[a] | | | DI virus 24 h after infection[b] | | |
|---|---|---|---|---|---|---|---|---|---|
| | Weight | Sick | Dead | Weight | Sick | Dead | Weight | Sick | Dead |
| 0 | 112 | 0 | 0 | 115 | 0 | 0 | 46 | 0 | 0 |
| 1 | 110 | 0 | 0 | 115 | 0 | 0 | 46 | 0 | 0 |
| 2 | 108 | 0 | 0 | 113 | 0 | 0 | 46 | 0 | 0 |
| 3 | 99 | 4 | 0 | 106 | 0 | 0 | 45 | 0 | 0 |
| 4 | 94 | 5 | 0 | 110 | 0 | 0 | 47 | 0 | 0 |
| 5 | 88 | 3 | 3 | 112 | 1 | 0 | 48 | 0 | 0 |
| 6 | 44 | 1 | 2 | 105 | 4 | 0 | 49 | 0 | 0 |
| 7 | 13 | | 1 | 100 | 3 | 1 | 50 | 0 | 0 |
| 8 | | | | 84 | 3 | 0 | 51 | 0 | 0 |
| 9 | | | | 81 | 4 | 0 | 51 | 0 | 0 |
| 10 | | | | 80 | 3 | 1 | 53 | 0 | 0 |
| 11 | | | | 68 | 2 | 0 | 53 | 0 | 0 |
| 12 | | | | 69 | 2 | 0 | 52 | 0 | 0 |
| 13 | | | | 70 | 1 | 0 | 53 | 0 | 0 |
| 14 | | | | 70 | 1 | 0 | 54 | 0 | 0 |
| 15 | | | | 71 | 1 | 0 | 55 | 0 | 0 |
| 16 | | | | 75 | 1 | 0 | 56 | 0 | 0 |
| 17 | | | | 75 | 1 | 0 | 57 | 0 | 0 | iDI, UV-inactivated defective interfering virus; DI virus, defective interfering virus.
[a] 6 mice/group;
[b] 2 mice/group).

All infected mice treated with control DI virus lost weight and most were ill by day 4. All mice were dead or were culled by day 7.

Infected mice treated with DI virus lost weight and suffered some delayed clinical disease which occurred over an extended period. Two mice died (days 7 and 10), and the rest (67%) recovered/were recovering.

EXAMPLE 10

Treatment of Mice with 244/PR8 DI Virus 48 h after Infection

As described in Example 8, but infected mice were given one dose of DI virus 48 h after infection.

Table 19 below shows the fate of mice given an intermediate dose (approximately 5 $MLD_{50}$ of infecting A/WSN virus, followed by administration of DI virus 48 h later against a control of administration of inactivated DI virus (both at 4000 HAU which is approximately 10 µg virus protein).

TABLE 19

| Day of infection | Virus + iDI virus 48 h after infection[a] | | | Virus + DI virus 48 h after infection[b] | | |
|---|---|---|---|---|---|---|
| | Weight | Sick | Dead | Weight | Sick | Dead |
| 0 | 109 | 0 | 0 | 139 | 0 | 0 |
| 1 | 108 | 0 | 0 | 141 | 0 | 0 |
| 2 | 111 | 0 | 0 | 142 | 0 | 0 |
| 3 | 107 | 0 | 0 | 138 | 0 | 0 |
| 4 | 99 | 4 | 0 | 133 | 0 | 0 |
| 5 | 90 | 4 | 1 | 136 | 0 | 0 |
| 6 | 71 | 4 | 0 | 131 | 2 | 0 |
| 7 | 69 | | 4 | 121 | 2 | 1 |
| 8 | | | | 97 | 5 | 0 |
| 9 | | | | 92 | 4 | 1 |
| 10 | | | | 73 | 3 | 2 |
| 11 | | | | 39 | 2 | 0 |
| 12 | | | | 39 | 2 | 0 |
| 13 | | | | 40 | 2 | 0 |
| 14 | | | | 42 | 1 | 0 |

TABLE 19-continued

| Day of infection | Virus + iDI virus 48 h after infection[a] | | | Virus + DI virus 48 h after infection[b] | | |
|---|---|---|---|---|---|---|
| | Weight | Sick | Dead | Weight | Sick | Dead |
| 15 | | | | 42 | 2 | 0 |
| 16 | | | | 44 | 2 | 0 |
| 17 | | | | 45 | 0 | 0 | iDI virus, UV-inactivated defective interfering virus; DI virus, defective interfering virus; g, weight in grams; numbers of sick/dead mice in each group occurring by day are shown. The (?) refers to mice that may have been ill, but were not definitely ill.
[a] 5 mice/group;
[b] 6 mice/group;
[c] 2 mice/group).

All infected mice treated with control inactivated DI virus lost weight, and were ill by day 5 after infection. All mice were dead by day 7.

Infected mice treated at 48 h after infection with DI virus lost weight, but illness was delayed and none was seen until day 6. Deaths (4/6) did not occur until days 7, 9 and 10. Two of 6 mice (33%) recovered fully.

EXAMPLE 11

244 iRNA Reduces Virus Yield

The 244 iRNA was cloned into the PolI expression plasmid pPOLI-SapIT, such that the vector expresses a vRNA-sense transcript. This was transfected into 293T cells along with the 12 plasmids required to generate infectious WSN virus. The DNA mix contained varying amounts of the 244 plasmid (0-0.5 µg), plus 0.5 µg of each WSN gene segment (under PolI promoters), 0.5 µg each PB1 and PB2 expression plasmids, 0.1 µg PA expression plasmid, and 1 µg NP expression plasmid. After 24 hr, the 293T cells were trypsinised, mixed with MDCK cells and re-plated. After a further 7 days the culture supernatant was harvested, and virus yield determined by HA assay.

TABLE 20

| 244 iRNA plasmid (µg) | Virus yield (HAU/ml) | Virus yield as % of control |
|---|---|---|
| 0 | 19200 | 100 |
| 0.1 | 9600 | 50 |
| 0.25 | 1600 | 8 |
| 0.5 | 300 | 1.6 |

Table 20 shows that as the amount of 244 plasmid increased, the total yield of virus as determined by HA decreased by 98.4%. Too much iRNA in the inoculum reduces the virus yield to unusable amounts.

EXAMPLE 12

Protecting Virus Prevents Clinical Disease but Allows Adaptive Immunity to the Challenge Virus to Develop Three weeks after mice were protected from 10 LD50 of A/WSN, they were rechallenged with a much higher dose of A/WSN (10,000 $LD_{50}$). This dose was used as it swamps even neat protecting virus (data not shown), and thus allows assessment of A/WSN-specific B and T cell immune responses. FIG. 3 (c, f, i) shows that all groups of surviving mice were completely immune to the rechallenge. As animals given 400 or 40 HAU of protecting virus showed no sign of disease during the primary challenge, their survival of the second high virus challenge shows that the mice developed protective immunity, and therefore that protecting virus effectively converts the initial lethal dose of virulent virus into a subclinical live vaccine. Table 21 below shows the highest dose of protecting virus provides only a weak vaccine effect. Counter intuitively, mice receiving the highest dose of protecting virus (4000 HAU) were less well protected from the second challenge, suggesting that virus replication and antigen production are so severely suppressed in this situation that the resulting infection is only weakly immunogenic.

TABLE 21

| | First challenge | | Second challenge | |
|---|---|---|---|---|
| Dose of protecting virus (HAU) | Number dead/number infected | Weight loss | Number ill/number challenged | Number dead/number challenged |
| 4000 | 0/7 | Yes | 5/7 (71%)[b] | 4/7 (57%)[c] |
| | 0/4 | Yes | 4/4 (100%) | 2/4 (50%) |
| | 0/4 | Yes | 4/4 (100%) | 3/4 (75%) |
| 400 | 0/4 | No | 0/4 | na |
| | 0/4 | No | 0/4 | na |
| 40 | 0/5 | No | 0/5 | na |
| | 0/4 | No | 0/4 | na |
| | 0/4 | No | 0/4 | na |
| 4 | 2/5 | No | 0/2 | na |
| 0[d] | 5/5 | na | Na | na |

[a]Mice were intranasally inoculated with a mix of protecting virus + 10 $LD_{50}$ challenge virus A/WSN (first challenge: columns 1 and 2); and then 3 weeks later inoculated with 10,000 $LD_{50}$ A/WSN alone (second challenge). This latter experiment tests adaptive immunity and not residual protecting virus activity, as the higher dose of A/WSN completely overcomes protecting virus when given simultaneously (not shown). Data from 3 separate experiments are shown.

[b]Mean = 87% ill.

[c]Mean = 60% dead.

[d]Given 4000 HAU of inactivated protecting virus.

Na, not applicable.

---

The invention claimed is:

1. A method for preventing or treating influenza A in a subject comprising administering an effective amount of a cloned defective interfering (DI) influenza A virus particle, wherein the cloned DI influenza A virus particle comprises an RNA segment 1 of the cloned DI influenza A virus;

further wherein the RNA segment 1 comprises a nucleic acid sequence consisting of (a) a sequence selected from SEQ ID NO: 1 or SEQ ID NO: 2; or (b) a nucleic acid sequence having at least 90% sequence identity with SEQ ID NO: 1.

2. The method of claim 1, wherein the cloned DI influenza A virus particle has antiviral effect in the subject.

3. The method of claim 1, wherein the influenza A in the subject is the same or a different strain or sub-type from the administered DI influenza A virus particle.

4. The method of claim 1, wherein the individual is infected with or has been in contact with another individual who is infected with an influenza A virus.

5. The method of claim 4, wherein the cloned DI influenza A virus is administered within 48 hours of the individual being infected or being in contact with the another individual who is infected with an influenza A virus.

6. The method of claim 5, wherein the cloned DI influenza A virus is administered within 24 hours of the individual being infected or being in contact with the another individual who is infected with an influenza A virus.

7. The method of claim 1, wherein the cloned DI influenza A virus is administered before the individual is exposed to a source of a live influenza A virus.

8. The method of claim 1, wherein the cloned DI influenza A virus particle genome RNA segment 1 nucleotide sequence consists of (a) a sequence selected from SEQ ID NO: 1 or SEQ ID NO: 2; or (b) a nucleic acid sequence having at least 95% sequence identity with SEQ ID NO: 1.

9. The method of claim 1, wherein the cloned DI influenza A virus particle genome RNA segment 1 nucleotide sequence consists of (a) a sequence selected from SEQ ID NO: 1 or SEQ ID NO: 2; or (b) a nucleic acid sequence having at least 99% sequence identity with SEQ ID NO: 1.

* * * * *

SEQUENCE LISTING

```
<160> NUMBER OF SEQ ID NOS: 5

<210> SEQ ID NO 1
<211> LENGTH: 395
<212> TYPE: DNA
<213> ORGANISM: Influenza A virus

<400> SEQUENCE: 1
agtagaaaca aggtcgtttt taaactattc gacactaatt gatggccatc cgaattcttt      60
tggtcgctgt ctggctgtca gtaagtatgc tagagtcccg tttccgtttc attaccaaca     120
ccacatcccc ttgcccaatt agcacattag ccttctctcc tttcgcaagg ttgctcagtt     180
cattgatgct tagtgctggc ccatatctct tgtcctcttt gcccagaatg aggaatcccc     240
tcagtcttct cctgtcttcc tgatgtgtac ttcttgatta tggccatatg gtccacggtg     300 gttttgtga gtatctcgcg ggtgcgagac tgcgacatta gatttcttag ttctttatt      360 ctttccatat tgaatatatt tgacctgctt tcgct                                395
```

```
<210> SEQ ID NO 2
<211> LENGTH: 395
<212> TYPE: DNA
<213> ORGANISM: Influenza A virus

<400> SEQUENCE: 2
agtagaaaca aggtcgtttt taaactattc gacactaatt gatggccatc cgaattcttt      60
tggtcgctgt ctggctgtca gtaagtatgc tagagtcccg tttccgtttc attaccaaca     120
ccacatcccc ttgcccaatt agcacattag ccttctctcc tttcgcaagg ttgctcagtt     180
cattgatgct tagtgctggc ccatatctct tgtcctcttt gcccagaatg aggaatcccc     240
tcagtcttct cctgtcttcc tgatgtgtac ttcttgatta tggccatatg gtccacggtg     300
gtttttgtga gtatctcgcg ggtgcgagac tgcgacatta gatttcttag ttcttttatt     360
ctttccatat tgaatataat tgacctgctt tcgct                                395

<210> SEQ ID NO 3
<211> LENGTH: 21
<212> TYPE: DNA
<213> ORGANISM: Artificial
<220> FEATURE:
<223> OTHER INFORMATION: type A influenza virus RNA1 forward primer
      RNA1F

<400> SEQUENCE: 3
agcgaaagca ggtcaaatat a                                                21

<210> SEQ ID NO 4
<211> LENGTH: 22
<212> TYPE: DNA
<213> ORGANISM: Artificial
<220> FEATURE:
<223> OTHER INFORMATION: type A influenza virus RNA1 reverse primer
      RNA1R

<400> SEQUENCE: 4
agtagaaaca aggtcgtttt ta                                               22

<210> SEQ ID NO 5
<211> LENGTH: 20
<212> TYPE: DNA
<213> ORGANISM: Artificial
<220> FEATURE:
<223> OTHER INFORMATION: type A influenza virus junction specific primer
      244J

<400> SEQUENCE: 5
atcccctcag tcttctcctg                                                  20
```